(12) United States Patent
Kim et al.

(10) Patent No.: US 11,881,097 B2
(45) Date of Patent: Jan. 23, 2024

(54) METHOD AND DEVICE FOR DETECTING FALL ACCIDENT BY USING SENSOR IN LOW POWER STATE

(71) Applicant: Samsung Electronics Co., Ltd., Gyeonggi-do (KR)

(72) Inventors: Hyeonseong Kim, Gyeonggi-do (KR); Jeonggwan Kang, Gyeonggi-do (KR); Chanung Park, Gyeonggi-do (KR); Seunghyuck Shin, Gyeonggi-do (KR)

(73) Assignee: Samsung Electronics Co., Ltd

( * ) Notice: Subject to any disclaimer, the term of this patent is extended or adjusted under 35 U.S.C. 154(b) by 443 days.

(21) Appl. No.: 16/944,794

(22) Filed: Jul. 31, 2020

(65) Prior Publication Data

US 2021/0035431 A1 Feb. 4, 2021

(30) Foreign Application Priority Data

Aug. 2, 2019 (KR) .................. 10-2019-0094587
Jul. 1, 2020 (KR) .................. 10-2020-0080825

(51) Int. Cl.
*G08B 23/00* (2006.01)
*G08B 21/04* (2006.01)
(Continued)

(52) U.S. Cl.
CPC ........ *G08B 21/0446* (2013.01); *A61B 5/0051* (2013.01); *A61B 5/1117* (2013.01);
(Continued)

(58) Field of Classification Search
CPC .................. G08B 21/0446; G08B 21/043; A61B 5/0051; A61B 5/1117; A61B 5/681; A61B 2560/0257; H04W 4/027
(Continued)

(56) References Cited

U.S. PATENT DOCUMENTS 8,494,507 B1 * 7/2013 Tedesco ................ G09B 21/00
455/418
9,402,568 B2 * 8/2016 Barfield ................ A61B 5/1117
(Continued)

FOREIGN PATENT DOCUMENTS

CN 104055518 9/2014
EP 3 003 147 3/2021
(Continued)

OTHER PUBLICATIONS

International Search Report dated Nov. 23, 2020 issued in counterpart application No. PCT/KR2020/010165, 8 pages.

*Primary Examiner* — Naomi J Small
(74) *Attorney, Agent, or Firm* — The Farrell Law Firm, P.C.

(57) ABSTRACT

Disclosed is an electronic device including an inertia sensor, an atmospheric pressure sensor, a processor operatively connected to the inertia sensor, the atmospheric pressure sensor, and a memory operatively connected to the processor, wherein the memory is configured to store instructions which, when executed, cause the processor to acquire acceleration sensing data from the inertia sensor and atmospheric pressure sensing data from the atmospheric pressure sensor, sense whether the electronic device has fallen based on the acceleration sensing data and the atmospheric pressure sensing data, and determine whether a user has fallen, based on the acceleration sensing data, when it is determined that the electronic device has fallen.

17 Claims, 17 Drawing Sheets

(51) Int. Cl.
  *A61B 5/11* (2006.01)
  *A61B 5/00* (2006.01)
  *H04W 4/02* (2018.01)
(52) U.S. Cl.
  CPC ............ *A61B 5/681* (2013.01); *G08B 21/043* (2013.01); *H04W 4/027* (2013.01); *A61B 2560/0257* (2013.01)
(58) Field of Classification Search
  USPC ...................................................... 340/573.1
  See application file for complete search history.

(56) References Cited

U.S. PATENT DOCUMENTS

| | | | |
|---|---|---|---|
| 2011/0261482 A1* | 10/2011 | Hirata | G11B 21/12 360/75 |
| 2014/0375461 A1 | 12/2014 | Richardson et al. | |
| 2015/0354967 A1* | 12/2015 | Matsushita | H04W 4/027 702/150 |
| 2016/0113551 A1 | 4/2016 | Annegam et al. | |
| 2016/0147965 A1* | 5/2016 | Matsumura | G16H 40/20 705/2 |
| 2018/0174420 A1* | 6/2018 | Clark | G01R 33/02 |
| 2019/0103007 A1 | 4/2019 | Tan et al. | |
| 2020/0258365 A1* | 8/2020 | Ten Kate | G08B 21/0446 |

FOREIGN PATENT DOCUMENTS

| | | |
|---|---|---|
| EP | 3 788 952 | 3/2021 |
| KR | 1020180082029 | 7/2018 |
| KR | 1020190056132 | 5/2019 |
| WO | WO 2018/127506 | 7/2018 |

\* cited by examiner (510)

(520)

(530)

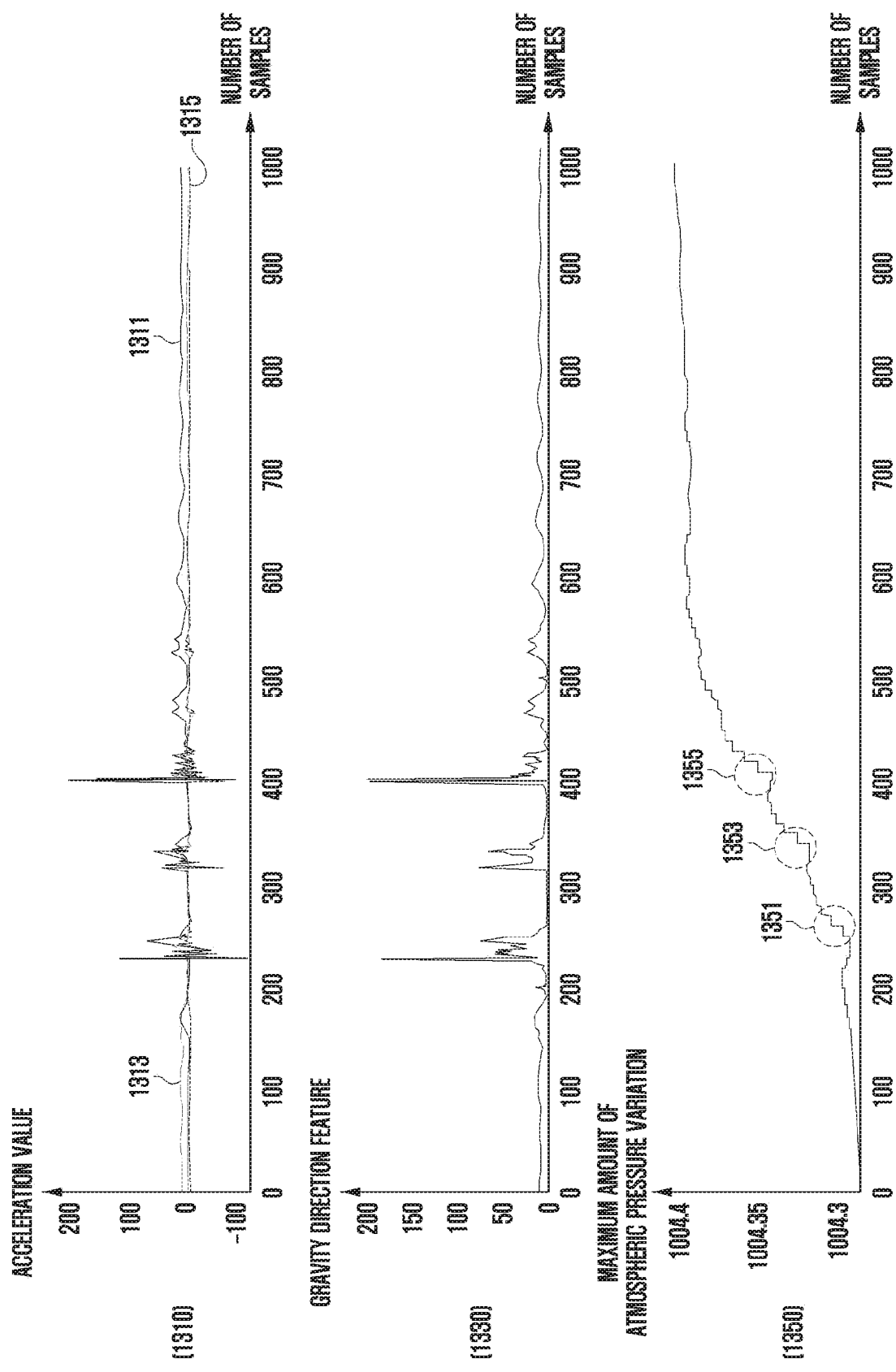

METHOD AND DEVICE FOR DETECTING FALL ACCIDENT BY USING SENSOR IN LOW POWER STATE

CROSS-REFERENCE TO RELATED APPLICATION(S)

This application is based on and claims priority under 35 U.S.C. § 119 to Korean Patent Application Nos. 10-2019-0094587 and 10-2020-0080825, filed on Aug. 2, 2019 and Jul. 1, 2020 respectively, in the Korean Intellectual Property Office, the entire content of each of which is incorporated herein by reference.

BACKGROUND

1. Field

The disclosure relates generally to an electronic device, and more particularly, to a method and electronic device for detecting a fall accident by using a sensor in a low power state.

2. Description of Related Art

With the development of digital technology, various types of electronic devices, such as a mobile communication terminal, a personal digital assistant (PDA), an electronic organizer, a smart phone, a tablet personal computer (PC), and a wearable device, have been widely used. In order to support and improve functions of these electronic devices, hardware parts and/or software parts thereof have been continuously developed.

For example, an electronic device can include a sensor that senses (or measures) various information (or data), and provides various information (or functions) based on sensing data acquired by the mounted sensor. For example, an electronic device can measure a bio-signal by using an electrode or a sensor, and provide various information related to a user's health, based on the measured bio-signal.

The electronic device may consume more electric power in order to acquire more accurate information by using a sensor. For example, when recognizing that a user has fallen by detecting the impulse using an acceleration sensor, a sampling rate of the sensor should be increased in order to accurately detect the impulse at a time when the user falls down and impacts the ground. When the sampling rate is increased, the consumed current to be added for a short time may not be large in view of a current battery capacity or a processor performance, but even though the sensor operates in a low power state, it may be problematic for the sensor to operate full-time, such as for 24 hours, to provide a service. Since an electronic device is designed to efficiently operate a limited resource, the sampling rate may not be unconditionally increased in order to accurately detect a time when an impact occurs.

In addition, a fall situation recognition method based on the impulse may cause misrecognition in various situations. For example, the electronic device may misrecognize when a user drops or generates an artificial impact on an electronic device as a situation in which the user has fallen. The electronic device may also misrecognize when the user quickly lowers the hand while wearing the electronic device, such as by hitting a piece of furniture while transporting the device or lying down on a soft surface, as situations in which the user has fallen.

Thus, there is a need in the art for a method and device that more accurately detect when a user has fallen.

SUMMARY

Aspects of the disclosure are to address at least the above-mentioned problems and/or disadvantages and to provide at least the advantages described below. Accordingly, an aspect of the disclosure is to provide a method and device for accurately recognizing when a user has fallen by sensing whether the user has fallen from sensing data acquired by an inertia sensor and an atmospheric pressure sensor and determining whether a result of the sensing is an error similar to a fall.

In accordance with an aspect of the disclosure, an electronic device includes an inertia sensor, an atmospheric pressure sensor, a processor operatively connected to the inertia sensor, the atmospheric pressure sensor, and a memory operatively connected to the processor, wherein the memory is configured to store instructions which, when executed, cause the processor to acquire acceleration sensing data from the inertia sensor and atmospheric pressure sensing data from the atmospheric pressure sensor, sense whether the electronic device has fallen based on the acceleration sensing data and the atmospheric pressure sensing data, and determine whether a user has fallen, based on the acceleration sensing data, when it is determined that the electronic device has fallen.

In accordance with another aspect of the disclosure, an operation method of an electronic device includes acquiring acceleration sensing data from an inertia sensor included in the electronic device and atmospheric pressure sensing data from an atmospheric pressure sensor included in the electronic device, sensing whether the electronic device has fallen based on the acceleration sensing data and the atmospheric pressure sensing data, and determining whether a user has fallen based on the acceleration sensing data, when it is determined that the electronic device has fallen.

BRIEF DESCRIPTION OF THE DRAWINGS

The above and other aspects, features and advantages of certain embodiments of the disclosure will be more apparent from the following detailed description, taken in conjunction with the accompanying drawings, in which:

FIG. 13A illustrates a sensor graph related to a fourth misrecognition improvement process.

DETAILED DESCRIPTION

Figure 1:
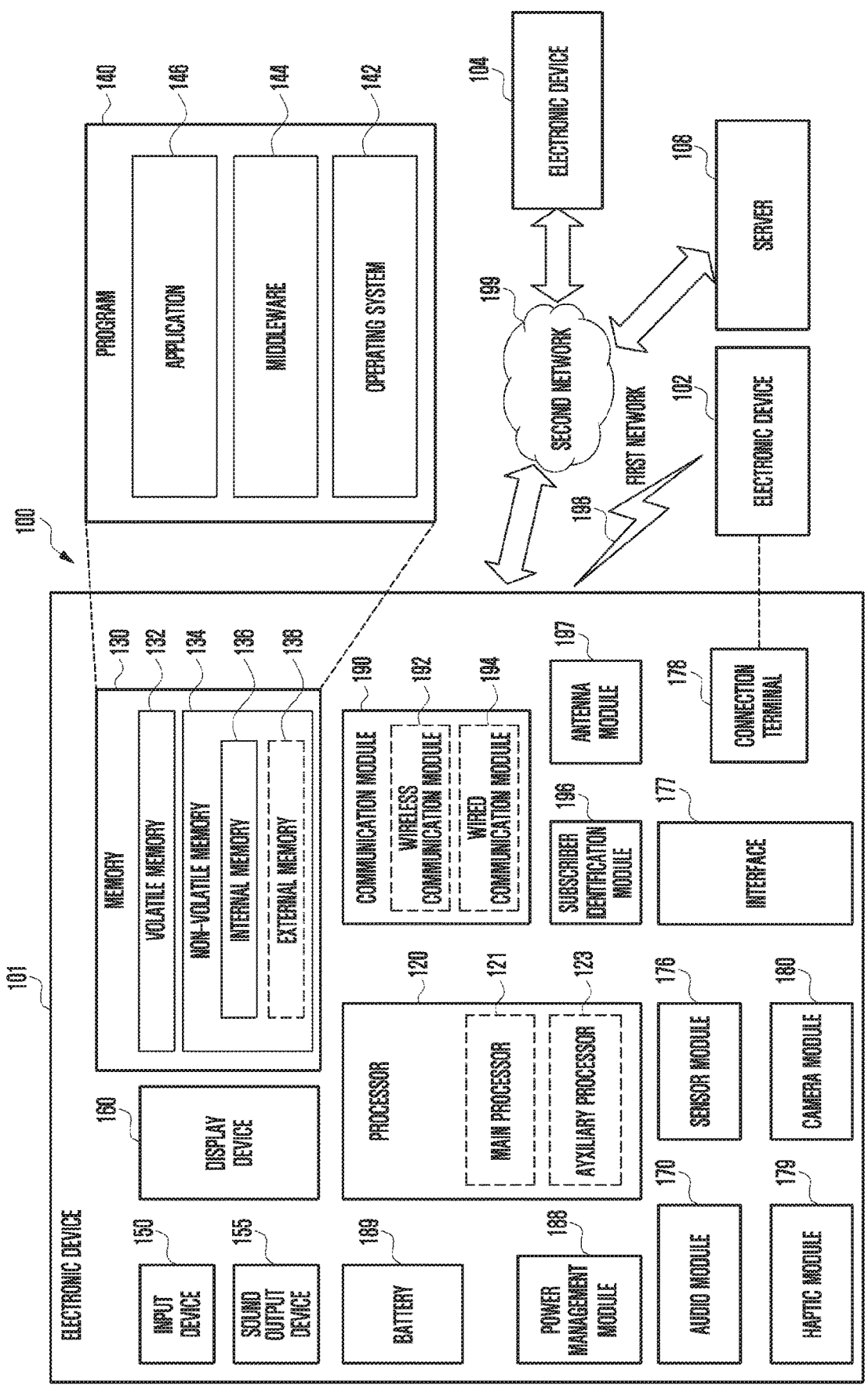
FIG. 1 is a block diagram of an electronic device 101 in a network environment, according to an embodiment.

Hereinafter, embodiments will be described in detail with reference to the accompanying drawings. Although specific embodiments are illustrated in the drawings and described in detail with reference thereto, this is not to limit the embodiments to specific forms. Detailed descriptions of known functions and/or configurations will be omitted for the sake of clarity and conciseness.

The electronic device according to various embodiments may be one of various types of electronic devices. The electronic devices may include, for example, and without limitation, a portable communication device (e.g., a smart phone), a computer device, a portable multimedia device, a portable medical device, a camera, a wearable device, a home appliance, or the like. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via a third element.

As used herein, the term "module" may include a unit implemented in hardware, software, or firmware, or any combination thereof, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

FIG. 1 is a block diagram illustrating an electronic device 101 in a network environment 100 according to various embodiments.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an example embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an ISP or a CP) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by another component (e.g., the processor 120) of the electronic device 101, from the outside (e.g., a user) of the electronic device 101. The input device 150 may include, for example, a microphone, a mouse, or a keyboard.

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector), The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, ISPs, or flashes.

The power management module 188 may manage power supplied to the electronic device 101. According to an example embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more CPs that are operable independently from the processor 120 (e.g., the AP) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include one or more antennas, and, therefrom, at least one antenna appropriate for a communication scheme used in the communication network, such as the first network 198 or the second network 199, may be selected, for example, by the communication module 190 (e.g., the wireless communication module 192). The signal or the power may then be transmitted or received between the communication module 190 and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

A method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2A:
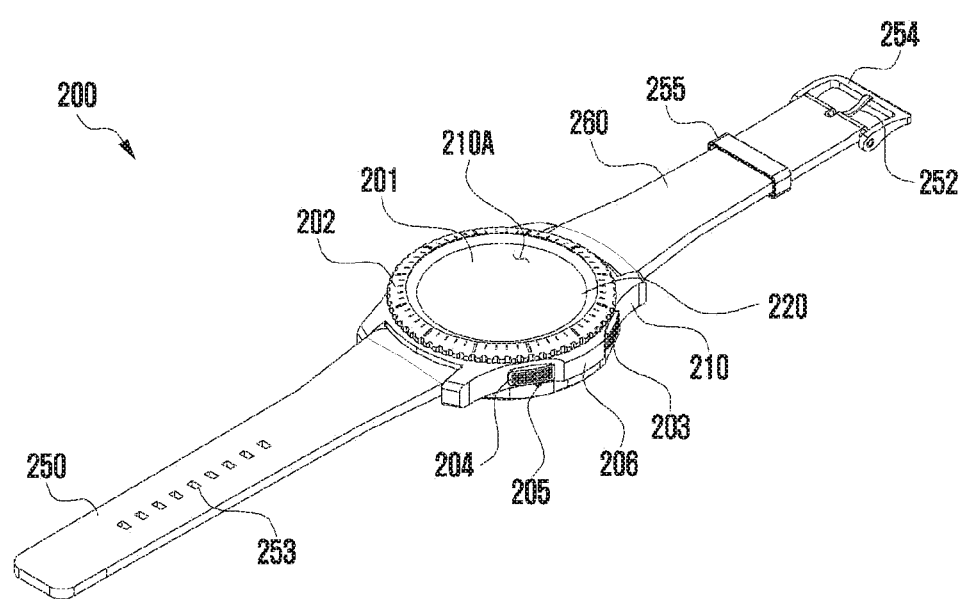
FIG. 2A is a front perspective view of an electronic device 200.
Figure 2B:
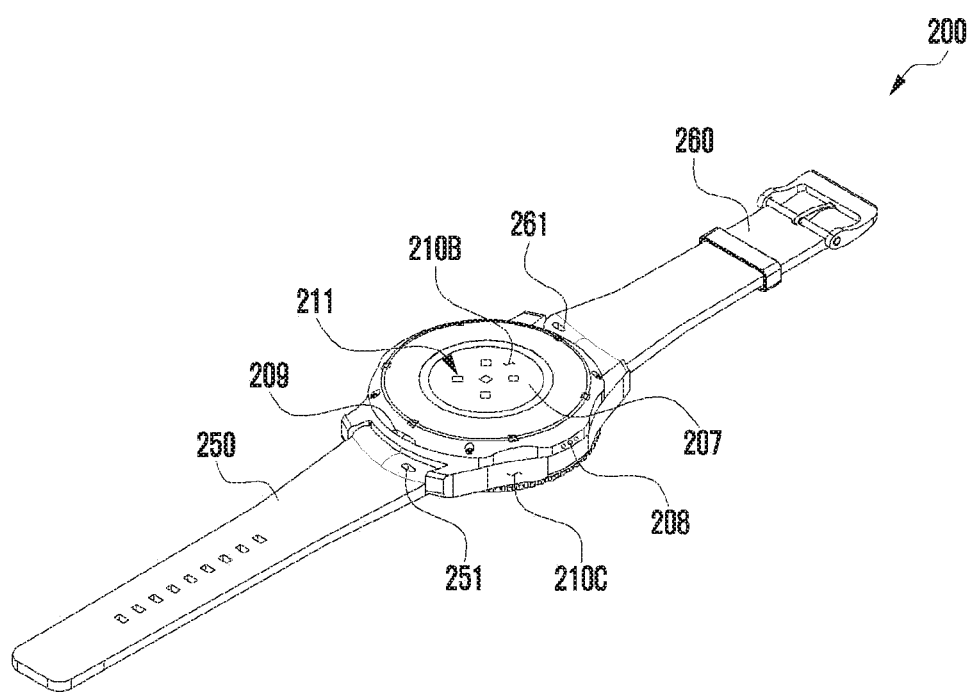
FIG. 2B is a rear perspective view of an electronic device 200 according to an embodiment.

FIG. 2A is a front perspective view illustrating an example electronic device 200 according to various embodiments, and FIG. 2B is a rear perspective view illustrating the example electronic device 200 according to various embodiments.

Referring to FIGS. 2A and 2B, an electronic device 200 according to an embodiment (e.g., an electronic device 101 of FIG. 1) may include a housing 210 including a first surface (or a front surface) 210A, a second surface (or a rear surface) 210B, and a side surface 210C that surrounds a space between the first surface 210A and the second surface 210B, and fastening members 250 and 260 (e.g., straps) connected to at least portions of the housing 210 and configured to detachably fasten the electronic device 200 to a portion (e.g., a wrist, or an ankle) of the body of a user. In another embodiment, the housing may refer to a structure that defines some of the first surface 210A, the second surface 210B, and the side surface 210C of FIG. 2A. According to an embodiment, the first surface 210A may be defined by a front plate 201 (e.g., a glass plate or a polymer plate including various coating layers), at least a portion of which is substantially transparent. The second surface 210B may be defined by a rear plate 207 that is substantially opaque. The rear plate 207, for example, may be formed of coated or colored glass, ceramics, a polymer, a metal (e.g., aluminum, stainless steel (STS), or magnesium), or a combination of at least two thereof. The side surface 210C may be coupled to the front plate 201 and the rear plate 207, and may be defined by a side bezel structure (or 'a side member') 206 including a metal and/or a polymer. In some embodiments, the rear plate 207 and the side bezel structure 206 may be integrally formed and may include the same material (e.g., a metallic material such as aluminum). The fastening members 250 and 260 may be formed of various materials and may have various shapes. A single body or a plurality of unit links that may move with respect to each other may be formed of woven fabric, leather, rubber, urethane, a metal, ceramics, or a combination of at least two thereof.

According to an embodiment, the electronic device 200 may include at least one of a display 220 (e.g., a display device 160 of FIG. 1), audio modules 205 and 208, a sensor module 211, key input devices 202, 203, and 204, and a connector hole 209. In some embodiments, at least one (e.g., the key input devices 202, 203, and 204, the connector hole 209, or the sensor module 211) of the elements may be omitted from the electronic device 200 or another component may be additionally included in the electronic device 200.

The display 220 (e.g., the display device 160 of FIG. 1, or a user interface), for example, may be exposed through a first part (e.g., a corresponding part of the front plate 201). The shape of the display 220 may correspond to the shape of the front plate 201, and may include various shapes, such as a circular shape, an elliptical shape, or a polygonal shape. The display 220 may be coupled to or be disposed to be adjacent to a touch detection circuit, a pressure sensor that may measure the strength (the pressure) of a touch, and/or a fingerprint sensor.

The audio modules 205 and 208 may include a microphone hole 205 and a speaker hole 208. A microphone for acquiring external sounds may be disposed in the microphone hole 205, and in some embodiments, a plurality of microphones may be disposed to detect the direction of a sound. The speaker hole 208 may be used for an external speaker and a communication receiver. In some embodiments, the speaker holes 207 and the microphone hole 203 may be realized by one hole or a speaker may be included while the speaker holes 207 are not employed (e.g., a piezoelectric speaker).

The sensor module 211 may generate an electrical signal or a data value corresponding to an operation state of the interior of the electronic device 200 or an environmental state of the outside. The sensor module 211, for example, may include a biometric sensor module (e.g., an HRM sensor) exposed through the second surface 210B of the housing 210. The biometric sensor module may include a photoplethysmogram (PPG) configured to calculate a blood pressure value while contacting a portion of the body of the user. The sensor module 211 may include an electrode that may measure at least one of an electrocardiogram (ECG), a galvanic skin response (GSR), an electroencephalogram (EEG), a bioimpedance assessment (BIA), or a ballistocardiogram (BCG). The sensor module 211 may further include at least one sensor. The electronic device 200 may further include a sensor module, for example, at least one of a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or an illumination sensor.

According to various embodiments, when the sensor module 211 may include a biometric optical sensor, an LED having various N wavelengths may be provided as a light source. When a green wavelength is used for the light source, the green wavelength may be a wavelength band that is most widely used to measure a heart rate, and the green wavelength may penetrate into skin thin and have robust characteristics to noise in the sensor module 211. When a red wavelength is used for the light source, the red wavelength may penetrate relatively deep skin and the sensor module 211 may measure a heart rate more precisely. When an infrared (IR) wavelength is used for the light source, the sensor module 211 may acquire biometric information such as a heart rate and a saturation of percutaneous oxygen (SPO2), together with the red wavelength. When the red, green, and ultraviolet wavelengths are used for the light source, the sensor module 211 may measure a skin tone. When the blue wavelength is used for the light source, the sensor module 211 may measure the tendency of blood glucose. As more various LED wavelengths are added, much more biometric information may be acquired.

According to various embodiments, the sensor module 211 may variously include one or more wavelengths. The sensor module 211 may include one or more emitters and detectors for the wavelengths. For example, the detectors may include one or more photodiodes, may be spaced apart from the light source by the same interval, and one or more detectors may be configured to have different spacing distances. A sensor IC may include a sensor driving controller that directly controls a sensor, and an analog-to-digital (A/D) converter. The sensor driving controller may include an emitter controller and a detector controller. The sensor driving controller may function to directly drive the emitter and the detector. The sensor driving controller may function as an analog front end (AFE). The analog front end may include LED drivers, an amplifier that amplifies detector values, an analog-to-digital converter that converts an analog value output from the detector to a digital value, and a controller that controls the LED drivers and the analog-to-digital converter. The sensor data input through the detector may be processed as biometric information and may be provided to the user. The biometric information may be stored in an application that provides biometric information, or may be provided in a third application.

The key input devices 202, 203, and 204 may include a wheel key 202 disposed on the first surface 210A of the housing 210 and being rotatable in at least one direction, and/or side key buttons 202 and 203 disposed on the side surface 210C of the housing 210. The wheel key may have a shape corresponding to the shape of the front plate 210. In another embodiment, the electronic device 200 may not include some or all of the above-mentioned key input devices 202, 203, and 204, and the key input devices 202, 203, and 204 which are not included, may be realized in different forms, such as a soft key, on the display 220. The connector hole 209 may accommodate a connector (e.g., a USB connector) for transmitting and receiving power and/or data to and from an external electronic device, and may include another connector hole that may accommodate a connector for transmitting and receiving an audio signal to and from an external electronic device. The electronic device 200, for example, may further include a connector cover configured to cover at least a portion of the connector hole 209 to prevent introduction of external foreign substances through the connector hole 109.

The fastening members 250 and 260 may be detachably fastened to at least a partial area of the housing 210 using locking members 251 and 261. The fastening members 250 and 260 may include one or more of a fixing member 252, a fixing member coupling hole 253, a band guide member 254, and a band fixing ring 255.

The fixing member 252 may be configured to fix the housing 210 and the fastening members 250 and 260 to a portion (e.g., a wrist or a wrinkle) of the body of the user. The fixing member coupling hole 253 may fix the housing 210 and the fastening members 250 and 260 to a portion of the body of the user in correspondence to the fixing member 252. The band guide member 254 may be configured to restrict a motion range of the fixing member 252 when the fixing member 252 is coupled to the fixing member coupling hole 253 so that the fastening members 250 and 260 are fastened to be attached to a portion of the body of the user. The band fixing ring 255 may restrict motion ranges of the fastening members 250 and 260 in a state in which the fixing member 252 and the fixing member coupling hole 253 are coupled to each other.

According to an embodiment, an electronic device (for example, the electronic device 101 of FIG. 1) according to various embodiments may include: an inertia sensor (for example, the sensor module 176 of FIG. 1 and the sensor module 211 of FIG. 2B); an atmospheric pressure sensor (for example, the sensor module 176 of FIG. 1 and the sensor module 211 of FIG. 2B); a processor (for example, the processor 120 of FIG. 1) operatively connected to the inertia sensor, the atmospheric pressure sensor, and a memory; and the memory (for example, the memory 130 of FIG. 1) operatively connected to the processor, wherein the memory may store instructions which, when executed, cause the processor to acquire acceleration sensing data from the inertia sensor and atmospheric pressure sensing data from the atmospheric pressure sensor, sense whether the electronic device has fallen, based on the acceleration sensing data and the atmospheric pressure sensing data, and determine whether a user has fallen, based on the acceleration sensing data, when it is determined that the electronic device has fallen.

The instructions may be further configured to extract a gravity direction feature from the acceleration sensing data, obtain an atmospheric pressure varying velocity or the maximum amount of atmospheric pressure variation from the atmospheric pressure sensing data, and sense whether the electronic device has fallen, based on at least one of the gravity direction feature, the atmospheric pressure varying velocity, and the maximum amount of atmospheric pressure variation.

When the electronic device moves with the direction of gravity (i.e., with gravity), the atmospheric pressure varying velocity exceeds a velocity threshold, and the maximum amount of atmospheric pressure variation exceeds a variation threshold, the instructions may be configured to determine that the electronic device has fallen, based on the extracted gravity direction feature.

The instructions may be further configured to sense the occurrence of the movement with gravity, with reference to the peak of the gravity direction feature, and determine that a fall has occurred in at least one of instances when the atmospheric pressure varying velocity exceeds a velocity threshold and the maximum amount of atmospheric pressure variation exceeds a variation threshold.

The instructions may be further configured to obtain an acceleration magnitude from the acceleration sensing data, detect a gravity-free section, based on the acceleration magnitude, and determine whether the user has fallen, based on the gravity-free section.

The instructions may be further configured to determine that the electronic device has fallen when the gravity-free section has a value exceeding a section threshold, and may be configured to determine that the user has had a fall accident when the gravity-free section has a value less than or equal to a section threshold.

The instructions may be further configured to obtain an acceleration magnitude from the acceleration sensing data, identify an impact timepoint (i.e., the time of impact), based on the acceleration magnitude, extract gravity direction features, based on the impact timepoint, calculate a difference value between the gravity direction features, and determine whether the user has fallen, based on the difference value.

The instructions may be further configured to determine that the electronic device has fallen when the difference value is less than or equal to a threshold, and may be configured to determine that the user has had a fall accident when the difference value exceeds the threshold.

The instructions may be further configured to determine an impact timepoint, based on the acceleration sensing data, calculate position information for a pre-impact time, based on the impact timepoint, calculate an amount of atmospheric pressure variation for a post-impact time, based on the impact timepoint, and determine that the electronic device has fallen when the position information has a value exceeding a configured threshold and the amount of atmospheric pressure variation exceeds a configured threshold.

The instructions may be further configured to determine that the user has had a fall accident when the position information or the amount of atmospheric pressure variation has a value less than or equal to a configured threshold.

The instructions may be further configured to determine an impact timepoint, based on the acceleration sensing data, divide a post-impact time into segments, based on the impact timepoint, calculate acceleration distribution for each segment and count the number of segments having the acceleration distribution having a value greater than or equal to a configured threshold, calculate a degree of atmospheric pressure variation for the post-impact time and count the number of valleys of the degree of atmospheric pressure variation, and determine that the electronic device has fallen when the counted number of segments exceeds a distribution reference value and the counted number of valleys exceeds a valley reference value.

The instructions may be further configured to calculate an average acceleration distribution for the post-impact time and determine that the electronic device has fallen when the average acceleration distribution has a value exceeding a configured threshold, the counted number of segments exceeds a distribution reference value, and the counted number of valleys exceeds a valley reference value.

The instructions may be further configured to determine that the user has had a fall accident when the counted number of segments is less than or equal to a distribution reference value or the counted number of valleys is less than or equal to a valley reference value.

The instructions may be further configured to calculate an average acceleration distribution for the post-impact time and determine that the user has had a fall accident when the average acceleration distribution has a value less than or equal to a configured threshold, the counted number of segments is less than or equal to a distribution reference value, or the counted number of valleys is less than or equal to a valley reference value.

The electronic device may further include a display (for example, the display device 160 of FIG. 1), a speaker (for example, the acoustic output device 155 of FIG. 1), or a vibration module (for example, the haptic module 179 of FIG. 1), wherein, when a situation is determined as a fall accident, the instructions may be configured to provide a notification related to a fall accident from at least one of the display, the speaker, or the vibration module.

After providing the notification, the instructions may be further configured to detect whether the electronic device moves, and provide different user interfaces, based on a result of the detection.

The electronic device may be a wearable device.

Figure 3:
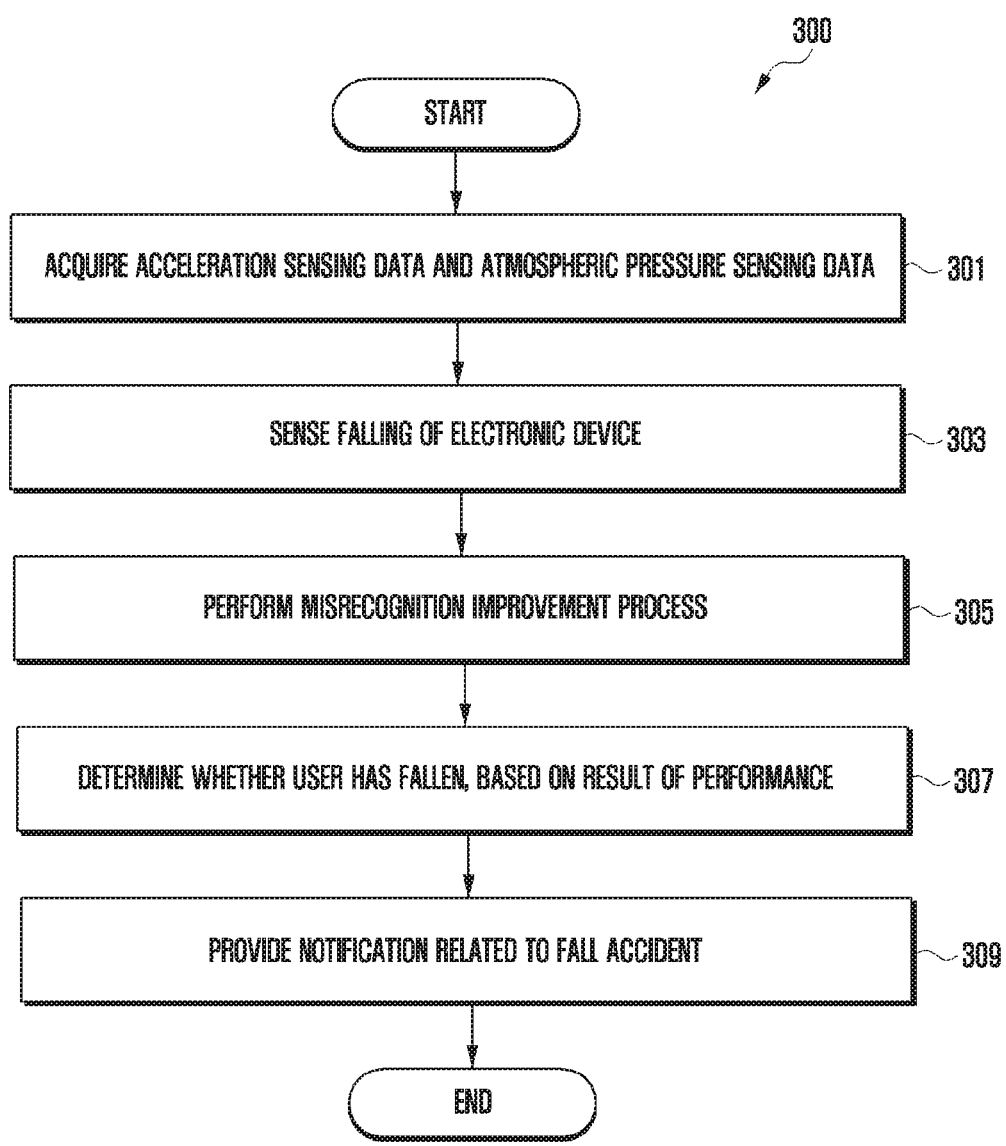
FIG. 3 is a flowchart illustrating an operation method of an electronic device according to an embodiment.

FIG. 3 illustrates an operation method of an electronic device according to an embodiment.

Referring to FIG. 3, in step 301, a processor of an electronic device may acquire (or collect) inertial sensing data (or acceleration sensing data) and atmospheric pressure sensing data from a sensor module. The acceleration sensing data may be acquired by an acceleration sensor, and the atmospheric pressure sensing data may be acquired by an atmospheric pressure sensor. The processor 120 may acquire the acceleration sensing data and the atmospheric pressure sensing data in real time, periodically, or selectively.

The acceleration sensing data may be acquired from an inertia sensor (for example, an acceleration sensor or a gyro sensor). Hereinafter, for convenience of description, the acceleration sensing data is described as being acquired from an acceleration sensor.

The processor 120 may store the acceleration sensing data and the atmospheric pressure sensing data in a memory 130 for a predetermined time (for example, 1 hour, 6 hours, 24 hours, or a week) in the memory 130 and may delete the stored acceleration sensing data and atmospheric pressure sensing data from the memory 130 after the predetermined time. In addition, the processor 120 may process the stored acceleration sensing data and atmospheric pressure sensing data into information requested by a user and then delete the stored acceleration sensing data and atmospheric pressure sensing data from the memory 130 after the predetermined time.

In step 303, the processor 120 may sense (or detect) the falling of the electronic device 101. The processor 120 may extract a gravity direction feature from the acceleration sensing data. The acceleration sensing data having been acquired from the acceleration sensor is a local frame value or coordinate corresponding to a relative coordinate system, and may have coordinates of the x-axis, the y-axis, and the z-axis. The processor 120 may convert the acceleration sensing data from a local frame to a navigation frame. The navigation frame corresponds to an absolute coordinate system, and may have coordinates corresponding to the East, West, North or South, an upward or downward, and diagonal direction. The processor 120 may extract an acceleration component of a direction perpendicular to the ground from the acceleration sensing data which has been converted into the navigation frame.

For example, the processor 120 may extract a value less than 0 from an upward value (or a value of the u-axis) of the acceleration sensing data having been converted into the navigation frame as the gravity direction feature. The processor 120 may remove a value greater than 0 from among components (for example, a component of the direction of gravity (i.e., with gravity)+a component of a direction opposite to the direction of gravity (i.e., against gravity)) of the vertical direction, the components being obtained through the upward value, and extract a value less than 0 as the gravity direction feature. The value greater than 0 may be a component of a direction (for example, an upward direction) against gravity, and the value less than 0 may be a component with gravity (for example, a downward direction). The gravity direction feature may include only the component with gravity, which is a value less than 0.

The processor 120 may calculate or measure an atmospheric pressure varying velocity or the maximum amount of atmospheric pressure variation from the atmospheric pressure sensing data. The processor 120 may obtain an atmospheric pressure varying velocity or the maximum amount of atmospheric pressure variation, based on an impact timepoint. The processor 120 may obtain an acceleration magnitude by using coordinates of the x-axis, the y-axis, and the z-axis of the acceleration sensing data. The processor 120 may obtain an acceleration magnitude from Equation (1), as follows:

$$\sqrt{x^2+y^2+z^2} \qquad (1)$$

x is coordinates of the x-axis of the acceleration sensing data, y is coordinates of the y-axis of the acceleration sensing data, and z is coordinates of the z-axis of the acceleration sensing data.

When a fall occurs, since the acceleration magnitude is to be detected to be high, the processor 120 may determine the peak of the acceleration magnitude as an impact timepoint.

The processor 120 may obtain an atmospheric pressure varying velocity or the maximum amount of atmospheric pressure variation for a predetermined time, such as a time interval from a pre-impact time to a post-impact time, with reference to the impact timepoint.

The atmospheric pressure varying velocity may be expressed by a gradient and the maximum amount of atmospheric pressure variation may be expressed in a peak-to-peak form. The atmospheric pressure varying velocity may indicate a gradient of atmospheric pressure variation for a predetermined time. The maximum amount of atmospheric pressure variation may indicate an amount of change between the lowest value and the highest value of the atmospheric pressure. The processor 120 may sense a situation as a fall situation when the atmospheric pressure varying velocity exceeds a velocity threshold and the maximum amount of atmospheric pressure variation exceeds a variation threshold.

The processor 120 may sense whether the fall situation occurs on further consideration of whether the movement is detected, based on the impact timepoint. The processor 120 may detect the movement of the electronic device 101 by using a motion sensor 176. The processor 120 may determine whether the detected movement is with gravity, based on the impact timepoint. For example, when the movement with gravity is detected, the atmospheric pressure varying velocity exceeds a velocity threshold, and the maximum amount of atmospheric pressure variation exceeds a variation threshold, the processor 120 may sense a situation as a fall.

When the atmospheric pressure varying velocity is less than or equal to a velocity threshold, and the maximum amount of atmospheric pressure variation exceeds a variation threshold, the processor 120 may sense that it is not a fall. In addition, when the movement with gravity is not detected, the atmospheric pressure varying velocity is less than or equal to a velocity threshold, and the maximum amount of atmospheric pressure variation exceeds a variation threshold, the processor 120 may sense that it is not a fall.

In step 305, the processor 120 may perform a fall misrecognition process. When the situation is sensed as a fall in step 303, the processor 120 may determine whether the sensed fall situation corresponds to a user's fall or the falling of the electronic device 101. The processor 120 may determine fall misrecognition, based on at least one of first to fourth misrecognition improvement processes. The first misrecognition improvement process may determine fall misrecognition based on a gravity-free section. The second misrecognition improvement process may determine fall misrecognition based on a difference value between gravity direction features after an impact timepoint. The third misrecognition improvement process may determine fall misrecognition based on position information and the maximum amount of atmospheric pressure variation, with reference to an impact timepoint. The fourth misrecognition improvement process may determine fall misrecognition based on acceleration distribution or a degree of atmospheric pressure variation with reference to an impact timepoint. When determining each of the first to fourth misrecognition improvement processes corresponds to a fall accident, the processor 120 may determine that a fall accident has occurred.

When determining each of the first to fourth misrecognition improvement processes corresponds to fall misrecognition, the processor 120 may determine that the electronic device 101 has fallen. When determining one of the first to fourth misrecognition improvement processes corresponds to fall misrecognition, the processor 120 may determine that the electronic device 101 has fallen. For example, even if a situation is determined as a fall accident by the first misrecognition improvement process, when a situation is determined as fall misrecognition by one of the second to fourth misrecognition improvement processes, the processor 120 may determine that the electronic device 101 has fallen. If a situation is determined as fall misrecognition by the first misrecognition improvement process or the third misrecognition improvement process, even when a situation is determined as a fall accident by the second misrecognition improvement process, the processor 120 may determine that the electronic device 101 has fallen. The processor 120 may determine fall misrecognition, based on the first to fourth misrecognition improvement processes, simultaneously, sequentially, or randomly.

The first misrecognition improvement process may obtain an acceleration magnitude from the acceleration sensing data, identify an impact timepoint, based on the acceleration magnitude, and detect a gravity-free section, based on the impact timepoint, so as to determine whether the detected gravity-free section has a value exceeding a section threshold. The processor 120 may determine that the electronic device 101 has fallen when the detected gravity-free section has a value exceeding a section threshold, and determine that a user has had a fall accident when the detected gravity-free section has a value less than or equal to a section threshold.

The second misrecognition improvement process may obtain an acceleration magnitude from the acceleration sensing data, determine an impact timepoint, based on the acceleration magnitude, extract gravity direction features, based on the impact timepoint, calculate a difference value between the gravity direction features, and determine whether the difference value is less than or equal to a threshold. The processor 120 may determine that a user has had a fall accident when the difference value exceeds a threshold, and determine the electronic device 101 has fallen when the difference value is less than or equal to a threshold.

The processor 120 may obtain a difference value between a first gravity direction feature extracted from first acceleration sensing data acquired after the impact timepoint and a second gravity direction feature extracted from second acceleration sensing data. The first gravity direction feature may convert the first acceleration sensing data into a navigation frame, and include only a component with gravity in an upward value of the converted first acceleration sensing data. The second acceleration sensing data may be acceleration sensing data acquired after the acquisition of the first acceleration sensing data. The second gravity direction feature may convert the second acceleration sensing data into a navigation frame, and include only a component with gravity in an upward value of the converted second acceleration sensing data. The processor 120 may repeatedly obtain a difference value between the gravity direction features for a predetermined time after the impact timepoint, determine that a user has had a fall accident when the obtained difference value exceeds a threshold, and determine that the electronic device 101 has fallen when the difference value is less than or equal to a threshold.

The third misrecognition improvement process may calculate position information for a pre-impact time, calculate the maximum amount of atmospheric pressure variation for a post-impact time when the calculated position information has a value exceeding a position threshold, determine that the user has had a fall accident when the maximum amount of atmospheric pressure variation exceeds a variation threshold, and determine that the electronic device 101 has fallen when the position information has a value less than or equal to the position threshold or the maximum amount of atmospheric pressure variation is less than or equal to the variation threshold.

The fourth misrecognition improvement process may divide the post-impact time into segments, calculate acceleration distribution for each segment, count the number of segments having the acceleration distribution having a value greater than or equal to a threshold, calculate a degree of atmospheric pressure variation for the post-impact time; count the number of valleys of the calculated degree of atmospheric pressure variation, determine that the user has had a fall accident when the counted number of segments is less than or equal to a distribution reference value or the counted number of valleys is less than or equal to a valley reference value, and determine that the electronic device 101 has fallen when the counted number of segments exceeds the distribution reference value and the counted number of valleys exceeds the valley reference value.

In step 307, the processor 120 may determine whether the user has had a fall accident, based on a result of the performance in step 305. The processor 120 may determine that the user has had a fall accident when a gravity-free section has a value less than or equal to a section threshold and a difference value between the gravity direction features having been extracted for a predetermined time after the impact timepoint exceeds a threshold. In addition, the processor 120 may identify that the electronic device 101 has fallen when a gravity-free section has a value exceeding a section threshold and a difference value between the gravity direction features having been extracted for a predetermined time after the impact timepoint exceeds a threshold. The processor 120 may identify that the electronic device 101 has fallen when a gravity-free section has a value less than or equal to a section threshold and a difference value between the gravity direction features exceeds a threshold.

The processor 120 may identify that the electronic device 101 has fallen when a gravity-free section has a value exceeding a section threshold and a difference value between the gravity direction features is less than or equal to a threshold. When it is determined that the electronic device 101 has fallen, the processor 120 may return to step 301, at which time the processor 120 may acquire acceleration sensing data and atmospheric pressure sensing data in real time or periodically and determine whether the user has had a fall accident.

The processor 120 may determine that the user has had a fall accident when the position information having been calculated for the pre-impact time has a value less than or equal to the position threshold. The processor 120 may determine that the user has had a fall accident when the position information has a value exceeding the position threshold and the maximum amount of atmospheric pressure variation having been calculated for the post-impact time exceeds the variation threshold. The processor 120 may determine that the electronic device 101 has fallen when the position information has a value exceeding the position threshold and the maximum amount of atmospheric pressure variation is less than the variation threshold.

The processor 120 may determine that the user has had a fall accident when the counted number of segments is less than or equal to the distribution reference value or the counted number of valleys is less than or equal to the valley reference value. The processor 120 may determine that the electronic device 101 has fallen when the counted number of segments exceeds the distribution reference value and the counted number of valleys exceeds the valley reference value.

In step 309, the processor 120 may provide a notification related to a fall accident on a display 160. The user interface may be configured to identify whether a fall accident occurs, inform the user of what to do if a fall accident occurs, or report the occurrence of a fall accident to an outside location. The processor 120 may provide a notification related to the fall accident from a speaker 155 or vibration from a haptic module 179.

The processor 120 may determine whether the movement of the electronic device 101 is detected for a predetermined time when a situation is sensed as the user's fall accident in step 307. The processor 120 may detect whether the electronic device 101 moves, by using a motion sensor. When the movement of the electronic device 101 is not detected for a predetermined time (for example, 30 minutes or 1 minute), namely in an inactivity situation, the processor 120 may determine the movement as the user's fall accident and provide a notification related to the fall accident.

Figure 4:
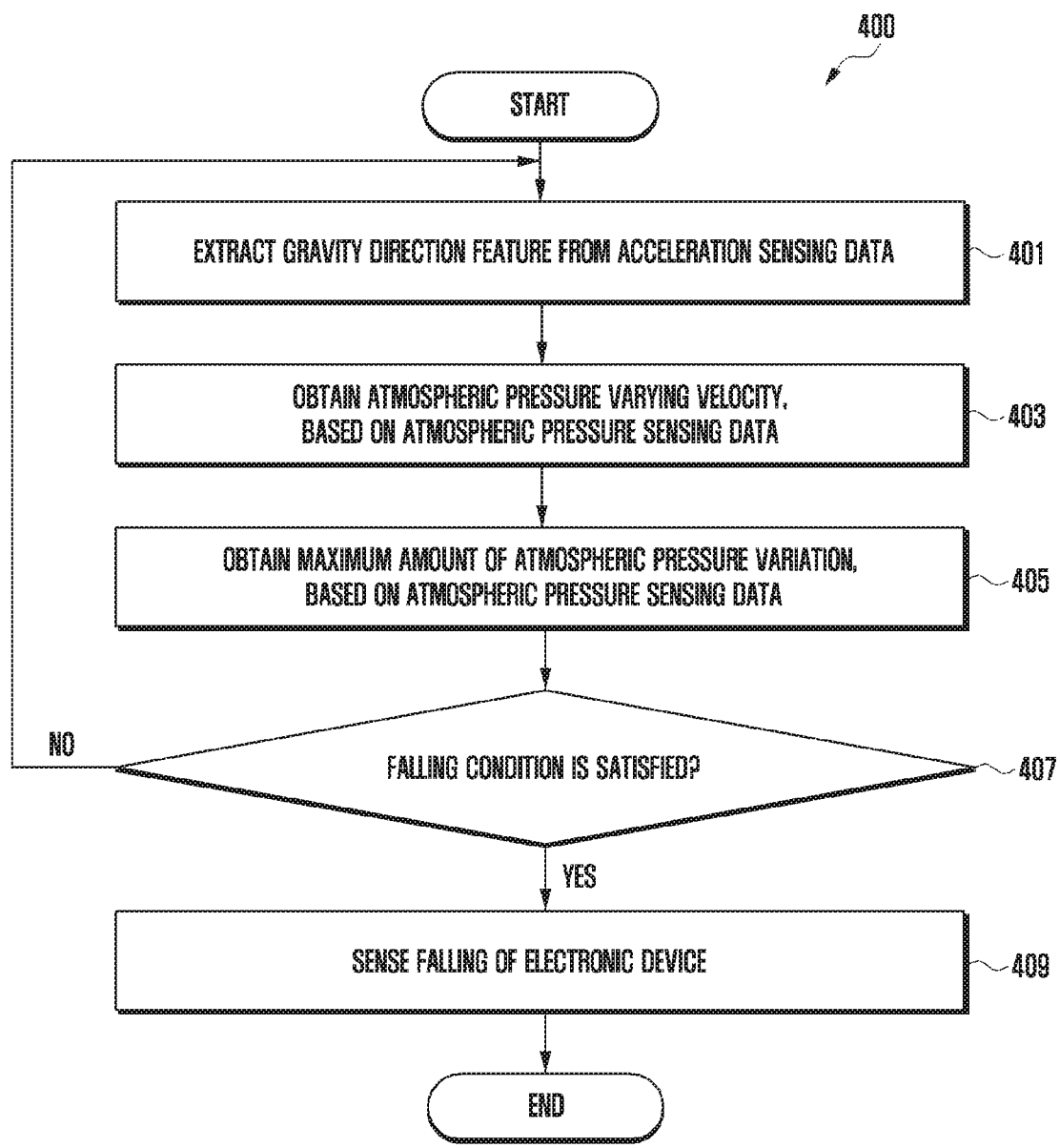
FIG. 4 is a flowchart illustrating a fall detection method of an electronic device according to an embodiment.

FIG. 4 is a flowchart 400 illustrating a fall detection method of an electronic device according to an embodiment. FIG. 4 may illustrate operation 303 of FIG. 3 in detail.

Referring to FIG. 4, in step 401, a processor of an electronic device may extract a gravity direction feature from acceleration sensing data. The acceleration sensing data having been acquired by the acceleration sensor is a local frame value corresponding to a relative coordinate system, and may have x-axis, the y-axis, and z-axis coordinates. The processor 120 may convert the acceleration sensing data from a local frame to a navigation frame. The navigation frame corresponds to an absolute coordinate system, and may have coordinates corresponding to the East, West, North, or South, an upward or downward and diagonal direction. The processor 120 may extract an acceleration component of a direction perpendicular to the ground from the acceleration sensing data which has been converted into the navigation frame. For example, the processor 120 may extract a value less than 0, as the gravity direction feature, from an upward value of the acceleration sensing data having been converted into the navigation frame.

The processor 120 may remove a value greater than 0 from among components (for example, a component with gravity+a component against gravity) of the vertical direction, the components being obtained through the upward value, and may extract a value less than 0 as the gravity direction feature. The value greater than 0 may be a component of a direction (for example, an upward direction) against gravity, and the value less than 0 may be a component with gravity (for example, a downward direction). The gravity direction feature may include only the component with gravity, which is a value less than 0.

In step 403, the processor 120 may obtain an atmospheric pressure varying velocity from the atmospheric pressure sensing data, based on an acceleration magnitude. The processor 120 may obtain an acceleration magnitude by using x-axis, y-axis, and z-axis coordinates of the acceleration sensing data. The processor 120 may obtain an acceleration magnitude from Equation (1).

While the user moves on the flat land while holding (or wearing) the electronic device 101, a variation of the acceleration magnitude may be low. However, when the user suddenly drops the electronic device 101 or has a fall accident, a variation of the acceleration magnitude may be high. The processor 120 may determine the peak of the acceleration magnitude as an impact timepoint. The atmospheric pressure varying velocity may be expressed by a gradient and indicate a gradient of the atmospheric pressure variation for a predetermined time. The processor 120 may obtain the atmospheric pressure varying velocity, based on the impact timepoint. The processor 120 may obtain the atmospheric pressure varying velocity for a predetermined time before, after, or at the impact timepoint.

In step 405, the processor 120 may obtain the maximum amount of atmospheric pressure variation from the atmospheric pressure sensing data based on the impact timepoint. The maximum amount of atmospheric pressure variation may be expressed in a peak-to-peak form. The processor 120 may obtain the maximum amount of atmospheric pressure variation for a predetermined time before, after, or at the impact timepoint.

In step 407, the processor 120 may identify (or determine) whether a falling condition is satisfied. The processor 120 may determine whether the falling condition is satisfied, based on the atmospheric pressure varying velocity and the maximum amount of atmospheric pressure variation. For example, the processor 120 may determine that the falling condition is satisfied when the atmospheric pressure varying velocity exceeds a velocity threshold and the maximum amount of atmospheric pressure variation exceeds a variation threshold. The velocity threshold or the variation threshold may be previously configured in the electronic device 101, based on the falling condition.

The processor 120 may determine whether the falling condition is satisfied, on further consideration of whether the movement with gravity is detected. The processor 120 may detect the movement of the electronic device 101 by using the sensor module 176. The processor 120 may determine whether the detected movement is with gravity, based on the impact timepoint. For example, the processor 120 may determine that the falling condition is satisfied when the movement with gravity is detected, the atmospheric pressure varying velocity exceeds a velocity threshold, and the maximum amount of atmospheric pressure variation exceeds a variation threshold.

The processor 120 may determine that the falling condition is not satisfied when the atmospheric pressure varying velocity is less than or equal to a velocity threshold, and the maximum amount of atmospheric pressure variation exceeds a variation threshold. In addition, the processor 120 may determine that the falling condition is not satisfied when the movement with gravity is not detected (e.g., such as when the movement against the direction of gravity is detected), the atmospheric pressure varying velocity is less than or equal to a velocity threshold, and the maximum amount of atmospheric pressure variation exceeds a variation threshold.

The processor 120 may determine whether the falling condition is satisfied on further consideration of the position information for the pre-impact time. The processor 120 may calculate position information for the pre-impact time, calculate the maximum amount of atmospheric pressure variation for the post-impact time when the calculated position information has a value exceeding a position threshold, and determine that the falling condition is satisfied when the position information has a value less than or equal to the position threshold or the maximum amount of atmospheric pressure variation is less than or equal to a variation threshold.

The processor 120 may determine whether the falling condition is satisfied on further consideration of acceleration distribution for each segment for the post-impact time. The processor 120 may divide the post-impact time into segments, calculate acceleration distribution for each segment; count the number of segments having the acceleration distribution having a value greater than or equal to a threshold, calculate a degree of atmospheric pressure variation for the post-impact time, count the number of valleys of the calculated degree of atmospheric pressure variation, and determine that the falling condition is satisfied when the counted number of segments exceeds a distribution reference value and the counted number of valleys exceeds a valley reference value.

When the falling condition is satisfied, the processor 120 may perform step 409 and, when the falling condition is not satisfied, return to step 401 and perform steps 401 to 407 in real time or periodically so as to sense whether the electronic device 101 has fallen.

When the falling condition is satisfied, in step 409, the processor 120 may determine that the electronic device 101 has fallen. When it is determined that the electronic device 101 has fallen, the processor 120 may determine whether the falling of the electronic device 101 is due to the user's fall accident or the falling of the electronic device 101. To this end, the processor 120 may perform step 305 of FIG. 3.

Figure 5:
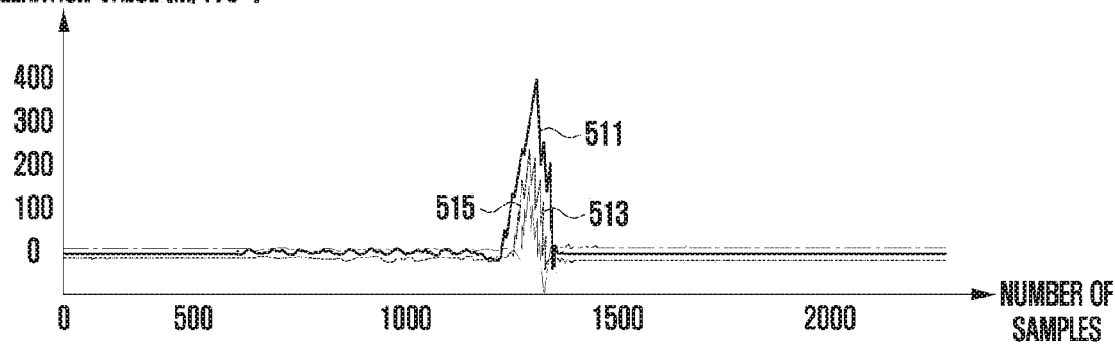
FIG. 5 illustrates a sensor graph related to fall detection according to an embodiment.
Figure 5:
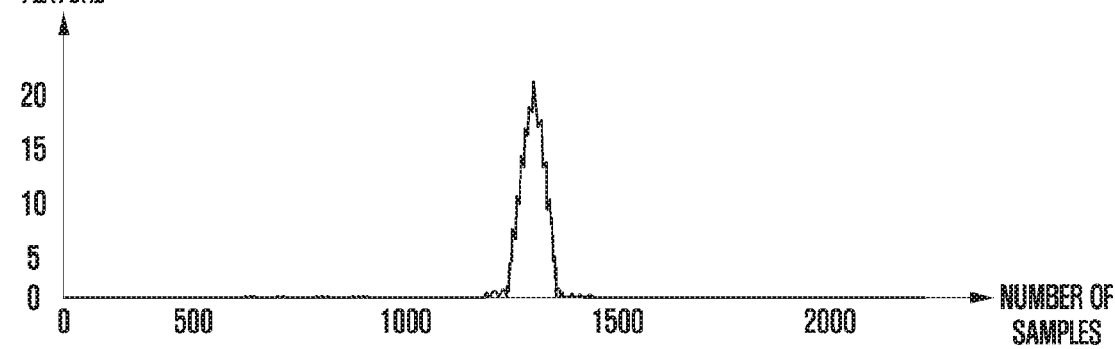
Figure 5:
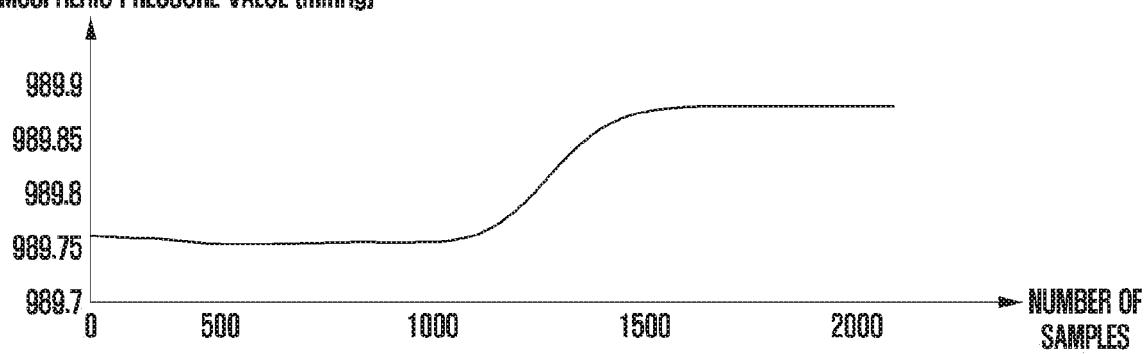

FIG. 5 illustrates a sensor graph related to fall detection according to an embodiment.

Referring to FIG. 5, a first graph 510 may represent acceleration sensing data (or an acceleration value) acquired by an acceleration sensor. The x-axis of the first graph 510 may indicate the number of samples and the y-axis thereof may indicate an acceleration value. For reference, one interval of the x-axis may indicate one sample, and a time unit of one sample may be 10 milliseconds (msecs). The acceleration sensing data of the first graph 510 may include an x-axis signal 511, a y-axis signal 513, and a z-axis signal 515, which correspond to a local frame. In the first graph 510, a timepoint, such as the 1350th sample representing the peak of the acceleration sensing data may be an impact timepoint (or an impact sensing timepoint). A second graph 520 represents a gravity direction feature. The processor 120 may convert the acceleration sensing data of the first graph 510 into a navigation frame which corresponds to an absolute coordinate system, and may have coordinates corresponding to the East, West, North or South, and an upward or downward direction. In regard to an upward value (or the u-axis), a value greater than 0 may be a component of a direction (for example, an upward direction) against gravity, and a value less than 0 may be a component with gravity (for example, a downward direction).

The processor 120 may extract a component with gravity as the gravity direction feature, the component having a value less than 0, from the upward value of the acceleration sensing data having been converted into the navigation frame. The x-axis of the second graph 520 may indicate the number of samples and the y-axis thereof may indicate a gravity direction feature. For reference, one interval of the x-axis may indicate one sample, and a time unit of one sample may be 10 msecs.

In the disclosure, the y-axis of the second graph 520 may remove a value greater than 0 and represent a value (for example, a component with gravity) less than 0 as the absolute value by converting the value from a negative number to a positive number. In the second graph 520, a timepoint, such as the 1350th sample representing the peak of the gravity direction feature may be an impact timepoint. A third graph 530 represents atmospheric pressure sensing data (or an atmospheric pressure value) acquired by an atmospheric pressure sensor. In the third graph 530, a timepoint, such as the 1300th sample representing the maximum amount of variation of the atmospheric pressure sensing data may be an impact timepoint.

The atmospheric pressure sensor may have a delay of a sensing timepoint in accordance with a feature of the electronic device 101. The x-axis of the third graph 530 may indicate the number of samples and the y-axis thereof may indicate an atmospheric pressure value. For reference, one interval of the x-axis may indicate one sample, and a time unit of one sample may be 10 msecs. The third graph 530 indicates that the maximum amount of atmospheric pressure variation is detected at the same timepoint as a sensing timepoint of the acceleration sensor, but the atmospheric pressure sensing data may have a delay in comparison with the acceleration sensing data. The timepoint representing the maximum amount of variation of the atmospheric pressure sensing data, which is shown in the third graph 530, may vary according to the electronic device 101.

Figure 6:
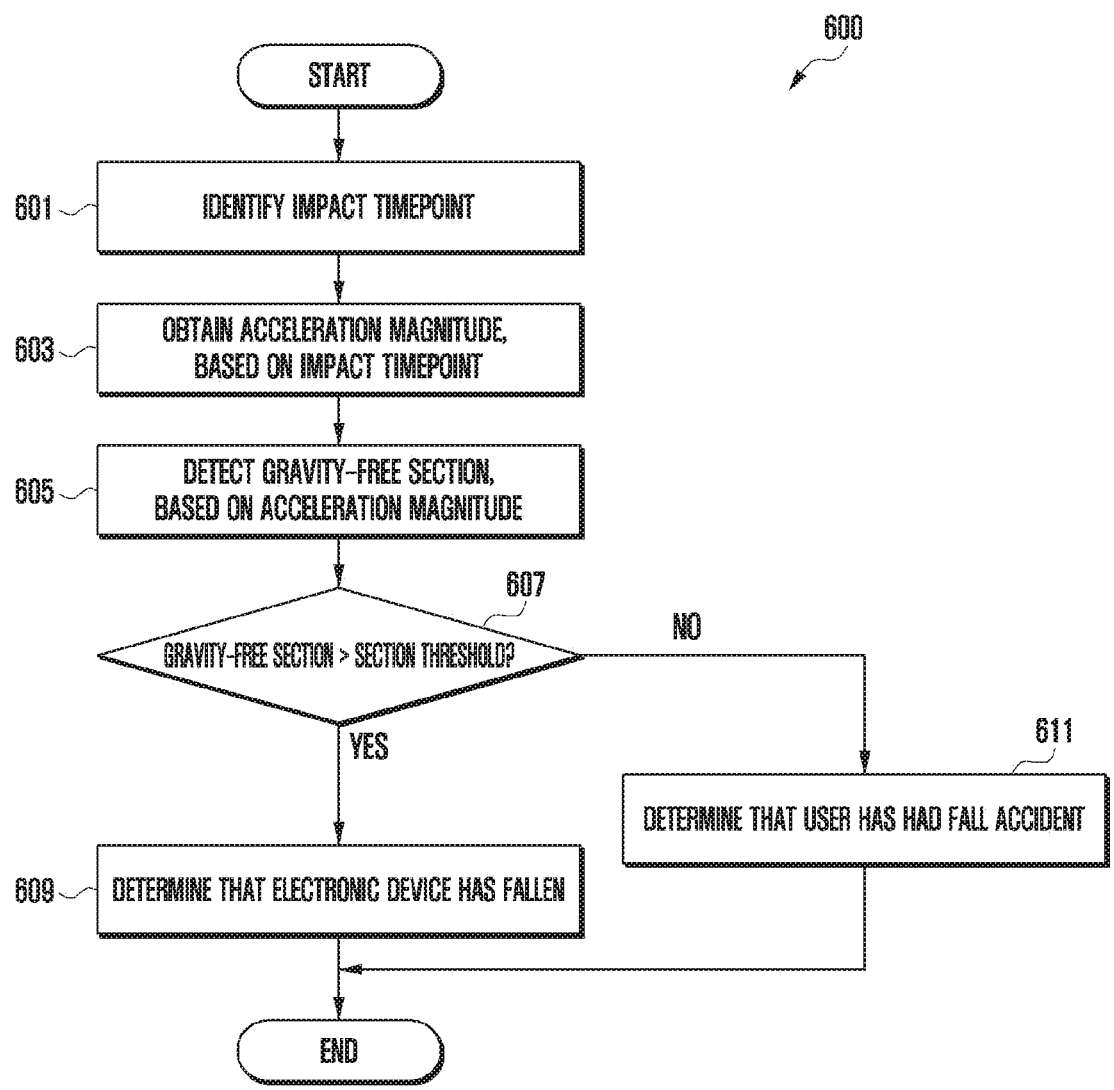
FIG. 6 is a flowchart illustrating a method for performing a first misrecognition improvement process in an electronic device according to an embodiment.

FIG. 6 is a flowchart 600 illustrating a method for performing a first misrecognition improvement process in an electronic device according to an embodiment. FIG. 6 may illustrate steps 305 and 307 of FIG. 3 in detail. The flowchart 600 of FIG. 6 may correspond to a first misrecognition improvement process.

Referring to FIG. 6, in step 601, a processor of an electronic device may identify an impact timepoint, based on acceleration sensing data. The processor 120 may obtain an acceleration magnitude by using a local frame value (e.g., x-axis, y-axis, and z-axis coordinates) of the acceleration sensing data. The processor 120 may obtain an acceleration magnitude from Equation (1). The processor 120 may determine a timepoint when a large variation in the acceleration magnitude occurs for a short time, as an impact timepoint. When the user suddenly drops the electronic device 101 or has a fall accident, the variation in the acceleration magnitude may be large.

In step 603, the processor 120 may extract acceleration magnitude for a predetermined time immediately before the impact timepoint. The processor 120 may obtain an acceleration magnitude for a predetermined time with reference to the impact timepoint. For example, the processor 120 may extract acceleration sensing data for the post-impact time (for example, 5 seconds or 10 seconds after the impact timepoint). The processor 120 may store the acceleration sensing data in a memory for a predetermined time (for example, 1 hour, 6 hours, 24 hours, and a week). The processor 120 may extract acceleration sensing data for the post-impact time from the acceleration sensing data stored in the memory 130. The processor 120 may obtain an acceleration magnitude for a predetermined time after the impact timepoint, by using the extracted acceleration sensing data.

In step 605, the processor 120 may detect a gravity-free section based on the acceleration magnitude. The gravity-free section may have an acceleration magnitude at or close to 0. Even if the user free-falls, the force may be applied to the electronic device at the moment when the user releases the electronic device, and the force may be applied to the x-axis or the y-axis rather than the z-axis. Since it is difficult to define a position of the electronic device 101 while the electronic device is falling, the processor 120 may detect a gravity-free section by using the acceleration magnitude without using information of each of the x-axis, the y-axis, and the z-axis of the acceleration sensing data. The gravity-free section may indicate that a timepoint when the acceleration magnitude becomes 0 does not temporarily appear, but appears for a predetermined time (for example, 0.5 seconds or 1 second). The processor 120 may identify (or determine) whether the gravity-free section is detected, based on the acceleration magnitude for the post-impact time.

The user may have a fall accident while wearing (or holding) the electronic device 101, or may drop the electronic device 101. Without any dynamics applied thereto, the electronic device 101 enters a gravity-free state while the electronic device 101 is falling, and the acceleration magnitude in the gravity-free state may become 0. However, when the user has a fall accident while wearing the electronic device 101 around the wrist, the user may consciously or unconsciously swing the arm or rotate, and thus the gravity-free section may not exist or may be detected for a very short time after the impact timepoint when a large variation in the acceleration magnitude is sensed.

For example, in a fall accident, an application of the dynamics occurs (for example, by the user's action of swinging the arm) in the electronic device 101, and thus a section in which the electronic device 101 enters a gravity-free state rarely exists or is detected for a very short time. On the other hand, when the electronic device 101 is dropped, an application of the dynamics does not occur in the electronic device 101. Therefore, only the force with gravity may be sensed. The electronic device 101 is in the gravity-free state in which only the force with gravity acts, and the gravity-free state may appear for a predetermined time.

In step 607, the processor 120 may identify (or determine) whether the gravity-free section has a value exceeding a section threshold. For example, the processor 120 may perform operation 609 when the gravity-free section has a value exceeding a section threshold (for example, 0.5 seconds), and perform step 611 when the gravity-free section has a value less than or equal to a section threshold.

When the gravity-free section has a value exceeding a section threshold, in step 609, the processor 120 may determine that the electronic device 101 has fallen. When the fall having been sensed in step 303 of FIG. 3 is determined to be the falling of the electronic device 101, the processor 120 returns to step 301 so as to acquire acceleration sensing data and atmospheric pressure sensing data in real time or periodically and thus determine whether the user has had a fall accident.

In addition, when a situation is determined as the falling of the electronic device 101 by a first misrecognition improvement process, the processor 120 may perform at least one of second to fourth misrecognition improvement processes. For example, in FIGS. 8, 10 and 12 to be described later herein, the processor 120 may omit steps 801 and 803 of FIG. 8 when performing the second misrecognition improvement process after performing the first misrecognition improvement process. The processor 120 may omit step 1001 of FIG. 10 when performing the third misrecognition improvement process after performing the first misrecognition improvement process. The processor 120 may omit step 1201 of FIG. 12 when performing the fourth misrecognition improvement process after performing the first misrecognition improvement process.

In reference again to FIG. 3, when a situation is determined as the falling of the electronic device 101 by the first to fourth misrecognition improvement processes, the processor 120 returns to step 301 so as to acquire acceleration sensing data and atmospheric pressure sensing data in real time or periodically and thus determine whether the user has had a fall accident. Even when a situation is determined as the falling of the electronic device 101 by the first misrecognition improvement process and a situation is determined as the user's fall accident by one of the second to fourth misrecognition improvement processes, the processor 120 may return to step 301. When a situation is determined as the falling of the electronic device 101 by the first misrecognition improvement process and a situation is determined as the user's fall accident by one of the second to fourth misrecognition improvement processes, the processor 120 may perform step 309 of FIG. 3.

Returning to FIG. 6, when the gravity-free section has a value less than or equal to a section threshold, in step 611, the processor 120 may determine that the user has had a fall accident. When the fall having been sensed in step 303 of FIG. 3 is determined to be the user's fall accident, the processor 120 performs step 309 of FIG. 3 so as to provide a notification related to a fall accident. Even when a situation is determined as the user's fall accident by the first misrecognition improvement process, the processor 120 may perform one of the second to fourth misrecognition improvement processes. The processor 120 may perform the second misrecognition improvement process, the third misrecognition improvement process, or the fourth misrecognition improvement process in sequence.

Figure 8:
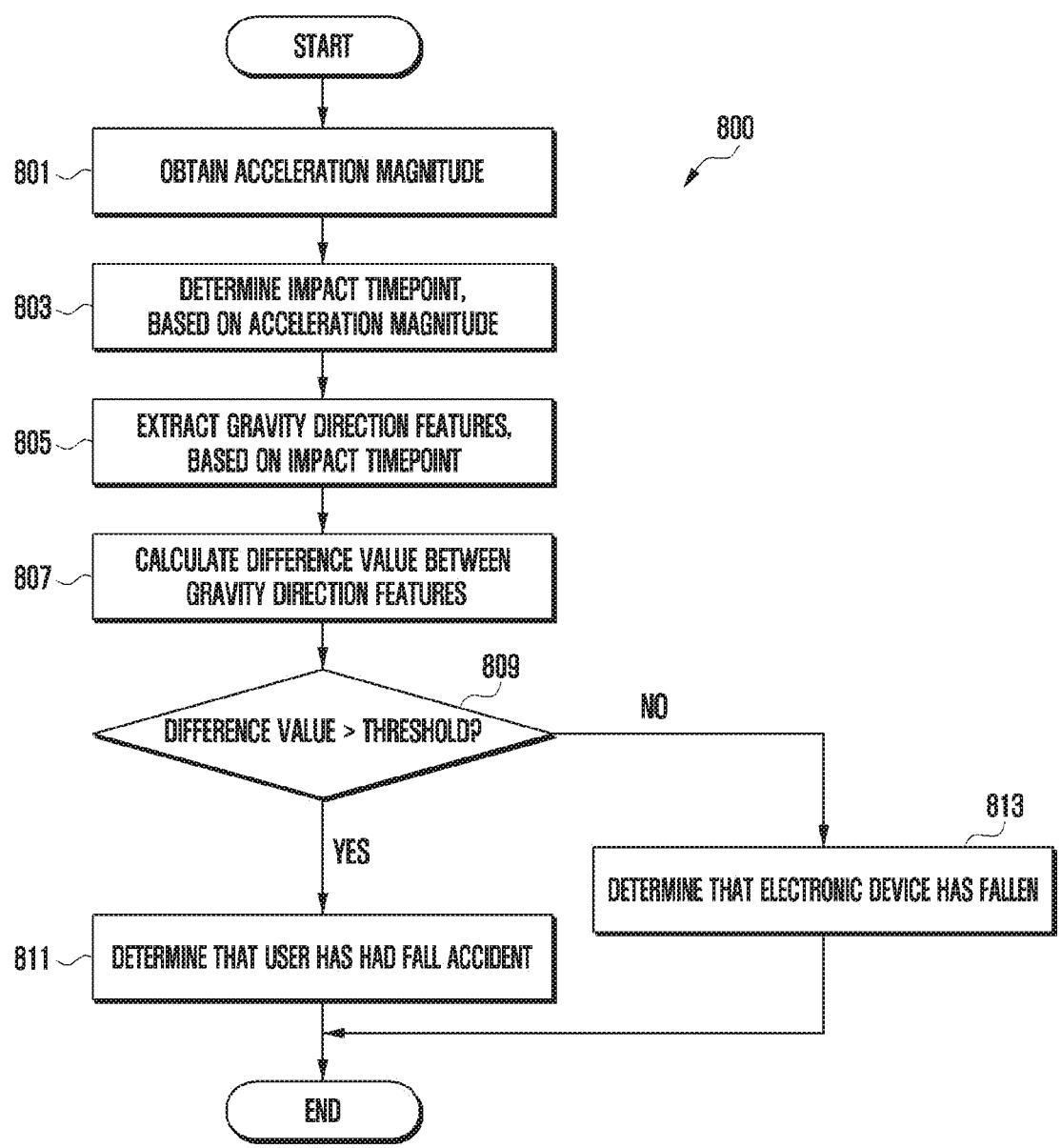
FIG. 8 is a flowchart illustrating a method for performing a second misrecognition improvement process in an electronic device according to an embodiment.

For example, in FIG. 8, the processor 120 may omit steps 801 and 803 when performing the second misrecognition improvement process after performing the first misrecognition improvement process, as 801 and 803 of FIG. 8 correspond to step 601 of FIG. 6.

Returning to FIG. 3, the processor 120 may perform step 309 when a situation is determined as the user's fall accident by the first to fourth misrecognition improvement processes. When it is determined that the user has had a fall accident, the processor 120 may provide a notification related to a fall accident in step 309. When a situation is determined as the user's fall accident by the first misrecognition improvement process and a situation is determined as the falling of the electronic device 101 by one of the second to fourth misrecognition improvement processes, the processor 120 may return to step 301.

the processor 120 may determine a misrecognition improvement process to be performed first in accordance with the user's configuration or a configuration of the electronic device 101. The processor 120 may configure the weight for each misrecognition improvement process, based on the user's history or a current state (or situation) of the electronic device 101. For example, the processor 120 may first perform the first misrecognition improvement process and then perform the third misrecognition improvement process, based on the configured weight. The processor 120 may first perform the second misrecognition improvement process, based on the configured weight, and then perform the fourth misrecognition improvement process.

Figure 7:
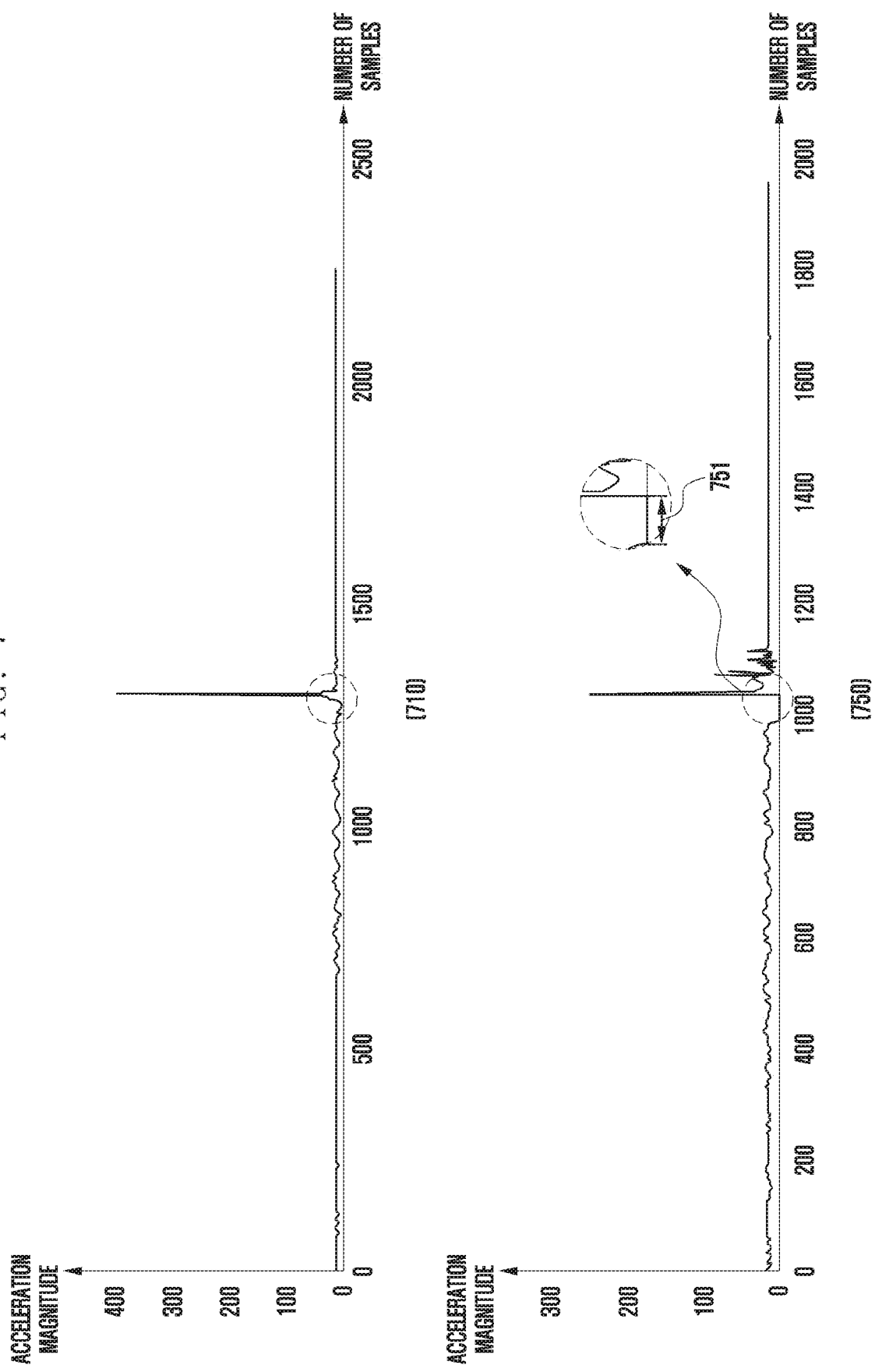
FIG. 7 illustrates a sensor graph related to a first misrecognition improvement process according to an embodiment.

FIG. 7 illustrates a sensor graph related to a first misrecognition improvement process according to an embodiment.

Referring to FIG. 7, a first graph 710 represents an acceleration magnitude when a user falls down while holding (or wearing) an electronic device. The x-axis of each of the first graph 710 and a second graph 750 may indicate the number of samples and the y-axis thereof may indicate an acceleration magnitude. For reference, one interval of the x-axis may indicate one sample, and a time unit of one sample may be 10 msecs. The acceleration magnitude is obtained by using the x-axis, y-axis, and z-axis coordinates of the acceleration sensing data, such as from Equation (1).

When the user falls down, since an application of the dynamics occurs (for example, by the user's action of swinging the arm) in the electronic device 101, as shown in a falling section (for example, the circle marked by a dotted line), a section in which the electronic device 101 becomes a gravity-free state rarely exists or is detected for a very short time. The second graph 750 indicates an acceleration magnitude when the user drops the electronic device 101. In this case, since an application of the dynamics does not occur in the electronic device 101, the electronic device 101 may enter a gravity-free state while falling. As shown in a falling section (for example, the circle marked by a dotted line) of the second graph 750, the gravity-free state having the acceleration magnitude of 0 while the electronic device 101 is falling may be expressed as a section 751.

The processor 120 may detect whether to misrecognize the fall in accordance with whether the gravity-free section is detected at the impact timepoint. The processor 120 may determine that the user has had a fall accident when the gravity-free section is not detected at the impact timepoint. The processor 120 may detect the falling of the electronic device 101 in accordance with whether the gravity-free section is detected at the impact timepoint or the gravity-free section has a value exceeding a section threshold. The processor 120 may determine that the electronic device 101 has fallen when the gravity-free section is detected at the impact timepoint or the gravity-free section has a value exceeding a section threshold.

FIG. 8 is a flowchart 800 illustrating a method for performing a second misrecognition improvement process in an electronic device according to an embodiment. FIG. 8 may illustrate steps 305 and 307 of FIG. 3 in detail. The flowchart 800 of FIG. 8 may correspond to the second misrecognition improvement process.

Referring to FIG. 8, in step 801, a processor of an electronic device may obtain an acceleration magnitude, based on acceleration sensing data. The processor 120 may obtain an acceleration magnitude by using a local frame value (for example, the x-axis, y-axis, and z-axis coordinates) of the acceleration sensing data. The processor 120 may obtain an acceleration magnitude from Equation (1).

In step 803, the processor 120 may determine an impact timepoint, based on the acceleration magnitude. When the user suddenly drops the electronic device 101 or has a fall accident, a variation in the acceleration magnitude may be large. The processor 120 may determine the peak of the acceleration magnitude as an impact timepoint.

In step 805, the processor 120 may extract a gravity direction feature, based on the impact timepoint. The processor 120 may extract a gravity direction feature by using the acceleration sensing data acquired for a predetermined time after the impact timepoint. For example, the processor 120 may obtain a difference value between a first gravity direction feature extracted from first acceleration sensing data acquired after the impact timepoint and a second gravity direction feature extracted from second acceleration sensing data.

The first acceleration sensing data may be sensed (or measured) first before the second acceleration sensing data. The first gravity direction feature may include only a component with gravity in an upward value of the first acceleration sensing data having been converted into a navigation frame. The second acceleration sensing data may be sensed (or measured) after the sensing of the first acceleration sensing data. The second gravity direction feature may include only a component with gravity in an upward value of the second acceleration sensing data having been converted into a navigation frame. The processor 120 may extract one or more gravity direction features repeatedly for a predetermined time after the impact timepoint.

In step 807, the processor 120 may calculate a difference value between gravity direction features. When the user has a fall accident while wearing (or holding) the electronic device 101, the acceleration may occur with gravity, with reference to the impact timepoint. When a fall accident occurs, a difference value (for example, an acceleration magnitude) between the first gravity direction feature and the second gravity direction feature with reference to the impact timepoint may be greater than 0. In regard to the upward value, the gravity direction feature does not include a value (for example, a component against gravity) greater than 0 and includes a value (for example, a component with gravity) less than 0, and thus an obtained difference value between two gravity direction features may be greater than 0.

However, when the user quickly moves the electronic device 101 from top to bottom, the acceleration may occur in a direction against gravity, with reference to the impact timepoint. This may be due to a repulsive force acting when the electronic device 101 is artificially and rapidly moved from top to bottom. When the electronic device 101 is rapidly moved from top to bottom, a difference value (for example, an acceleration magnitude) between the first gravity direction feature and the second gravity direction feature with reference to the impact timepoint may be 0. In regard to the upward value, the gravity direction feature does not include a value (for example, a component against gravity) greater than 0, and thus may have a value of 0 when the force acts against gravity, such as a case in which a repulsive force acts. The processor 120 may detect whether to misrecognize a fall, based on the difference value between the gravity direction features.

For example, the processor 120 may obtain a first difference value between the first gravity direction feature and the second gravity direction feature. The first difference value may be obtained by subtracting the second gravity direction feature from the first gravity direction feature. For example, the processor 120 may obtain a second difference value between the second gravity direction feature and a third gravity direction feature having been extracted after the extraction of the second gravity direction feature. The second difference value may be obtained by subtracting the third gravity direction feature from the second gravity direction feature. The processor 120 may obtain a first difference value between a fourth gravity direction feature and the third gravity direction feature, which have been extracted after the extraction of the second gravity direction feature. The second difference value may be obtained by subtracting the fourth gravity direction feature from the third gravity direction feature. The processor 120 may repeatedly obtain one or more difference values for a predetermined time after the impact timepoint.

In step 809, the processor 120 may determine whether the calculated difference value exceeds a threshold. The processor 120 may determine whether at least one of the difference values exceeds a threshold. The processor 120 may perform step 811 when the difference value exceeds the threshold, and perform step 813 when the difference value is less than or equal to the threshold.

In step 811, the processor 120 may determine that the user has had a fall accident when the difference value exceeds the threshold. When the fall having been sensed in step 303 of FIG. 3 is determined to be the user's fall accident, the processor 120 may perform step 309 to provide a notification related to a fall accident. When a situation is determined as the user's fall accident by the second misrecognition improvement process, the processor 120 may perform at least one of the first misrecognition improvement process, the third misrecognition improvement process, or the fourth misrecognition improvement process.

The processor 120 may perform step 309 of FIG. 3 when a situation is determined as the user's fall accident by the first to fourth misrecognition improvement processes. The processor 120 may perform step 309 of FIG. 3 when a situation is determined as the falling of the electronic device 101 by the first misrecognition improvement process and a situation is determined as the user's fall accident by the second misrecognition improvement process.

Figure 10:
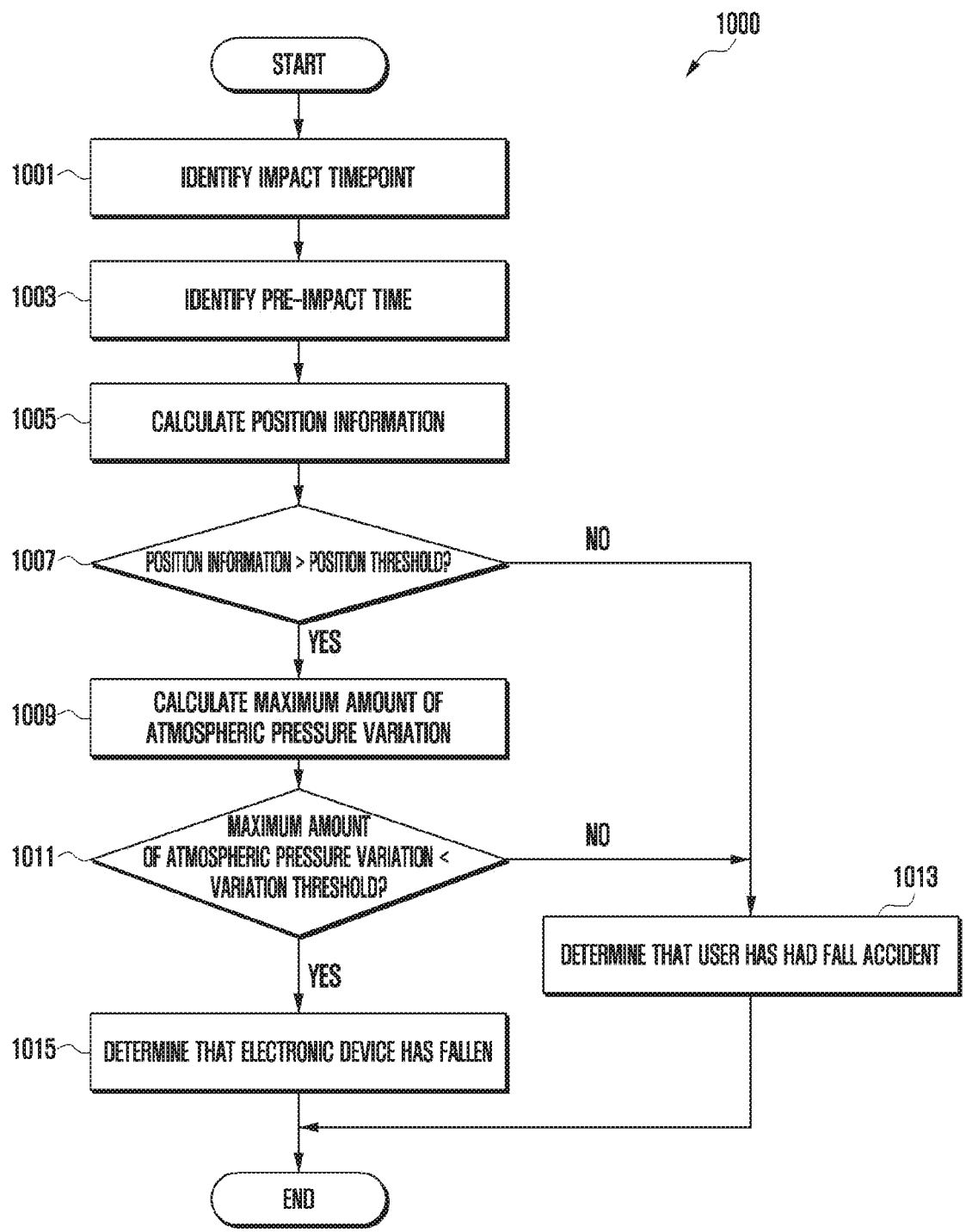
FIG. 10 is a flowchart illustrating a method for performing a third misrecognition improvement process in an electronic device according to an embodiment.
Figure 12:
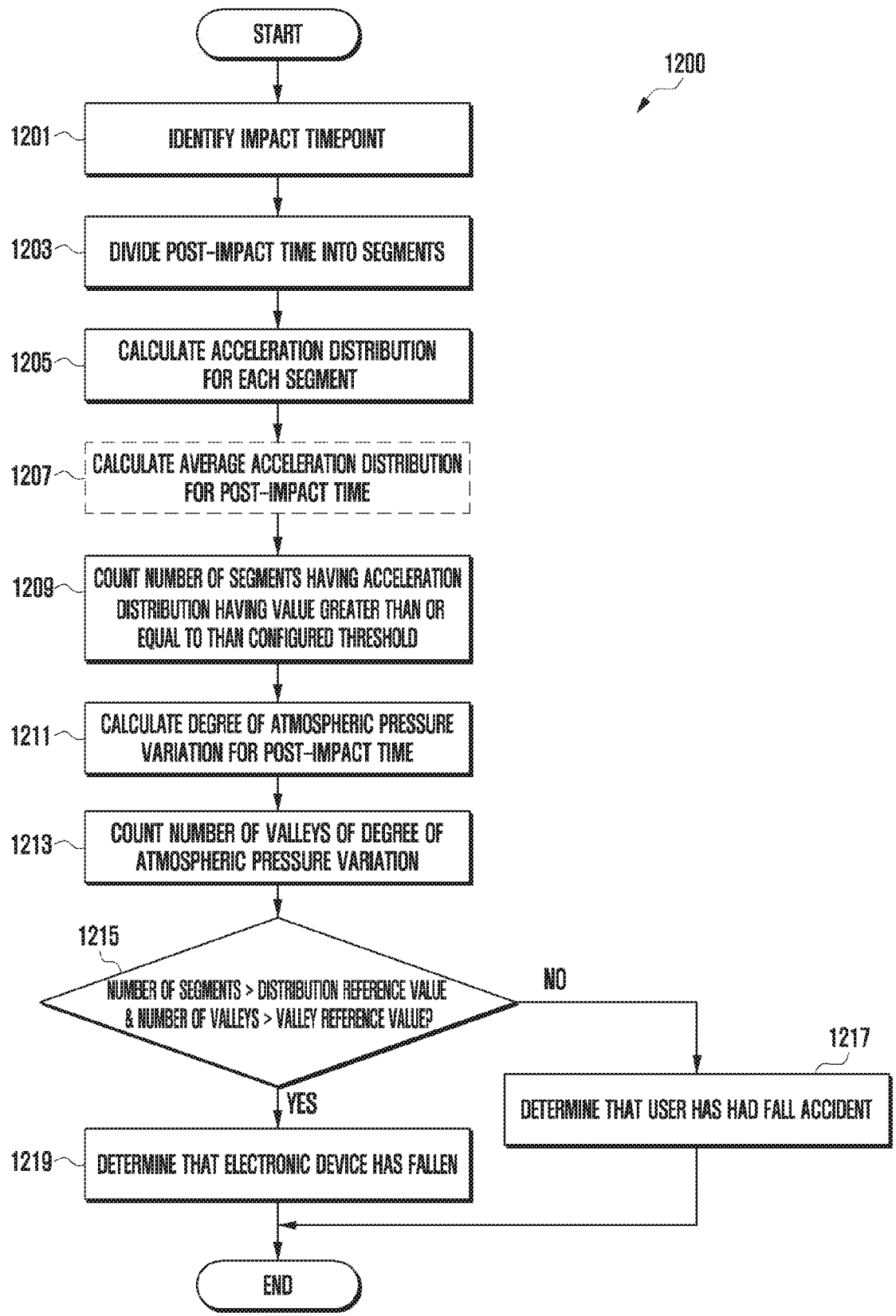
FIG. 12 is a flowchart illustrating a method for performing a fourth misrecognition improvement process in an electronic device according to an embodiment.

Returning to FIG. 8, in step 813, the processor 120 may determine that the electronic device 101 has fallen when the difference value is less than or equal to the threshold. When the fall having been sensed in step 303 of FIG. 3 is determined to be the falling of the electronic device 101, the processor 120 returns to step 301 so as to acquire acceleration sensing data and atmospheric pressure sensing data in real time or periodically and thus determine whether the user has had a fall accident. The processor 120 may perform the third misrecognition improvement process or the fourth misrecognition improvement process when a situation is determined as the falling of the electronic device 101 by the second misrecognition improvement process. In FIG. 6, the processor 120 may omit step 601 when performing the first misrecognition improvement process after performing the second misrecognition improvement process. In FIG. 10, the processor 120 may omit step 1001 when performing the third misrecognition improvement process after performing the second misrecognition improvement process. In FIG. 12, the processor 120 may omit step 1201 when performing the fourth misrecognition improvement process after performing the second misrecognition improvement process.

Referring back to FIG. 3, the processor 120 starts the method of FIG. 3 again so as to acquire acceleration sensing data and atmospheric pressure sensing data in real time or periodically and thus determine whether the user has had a fall accident, when a situation is determined as the falling of the electronic device 101 by the first misrecognition improvement process and a situation is determined as the falling of the electronic device 101 by the second misrecognition improvement process. The processor 120 may return to step 301 when a situation is determined as the user's fall accident by the first misrecognition improvement process and a situation is determined as the falling of the electronic device 101 by the second misrecognition improvement process.

The processor 120 may determine a misrecognition improvement process to be performed first in accordance with the user's configuration or a configuration of the electronic device 101. The processor 120 may configure the weight for each misrecognition improvement process, based on the user's history or a current state (or situation) of the electronic device 101. For example, the processor 120 may first perform the second misrecognition improvement process and then perform the fourth misrecognition improvement process, based on the configured weight. The processor 120 may first perform the first misrecognition improvement process, based on the configured weight, and then perform the third misrecognition improvement process.

Figure 9:
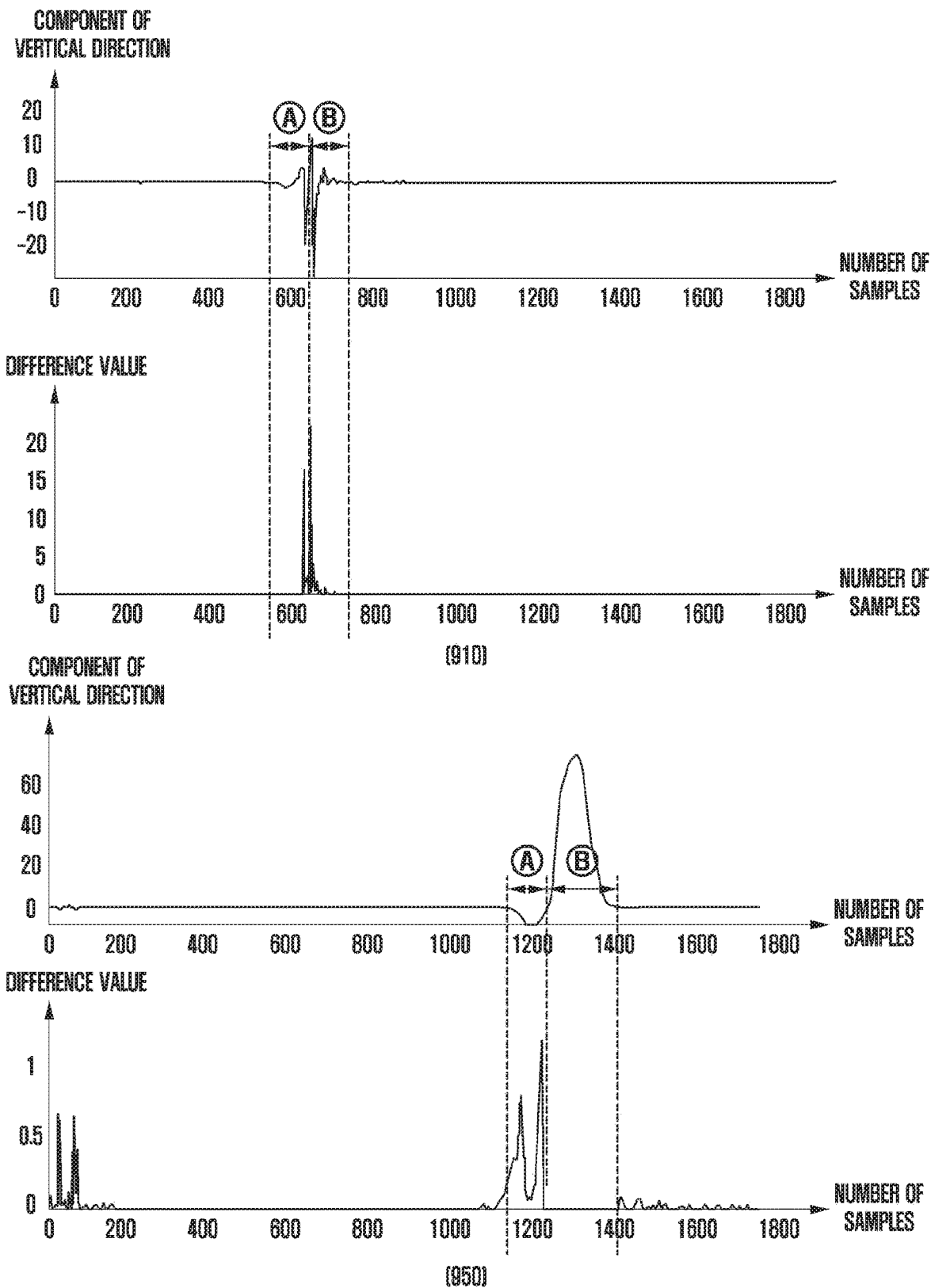
FIG. 9 illustrates a sensor graph related to a second misrecognition improvement process according to an embodiment.

FIG. 9 illustrates a sensor graph related to a second misrecognition improvement process according to an embodiment.

Referring to FIG. 9, a first graph 910 represents a component of the vertical direction and a difference value between gravity direction features when the user falls down while wearing (or holding) the electronic device 101. The x-axis of each of the first graph 910 and a second graph 950 may indicate the number of samples and one interval of the x-axis may indicate one sample, and a time unit of one sample may be 10 msecs. The component of the vertical direction indicates an upward value of the acceleration sensing data having been converted into a navigation frame, and may indicate a component of a direction perpendicular to the ground.

When the user falls down, the acceleration with gravity may occur before and after the impact timepoint. The second graph 950 represents a component of the vertical direction and a difference value between gravity direction features when the user rapidly moves the electronic device 101 from top to bottom. In the first graph 910 and the second graph 950, section A may indicate when the electronic device starts to fall, and then reaches and impacts the ground, in which instance the electronic device 101 falls, and section B may indicate a time since the impact timepoint, in which instance the electronic device 101 completely stops moving after reaching and impacting the ground. Section A has a value of less than or equal to 0 in the component of the vertical direction, and may include an impact timepoint.

It is noted from the first graph 910 that section B indicates that the acceleration occurs with gravity before and after the impact timepoint. It is noted that, in the component of the vertical direction of the first graph 910, a value less than 0 indicates the occurrence of the acceleration with gravity. It is noted from the second graph 950 that section B indicates the occurrence of the acceleration in a direction opposite to gravity. This may be because a repulsive force acts when the electronic device 101 is artificially and rapidly moved from top to bottom. It is noted that, in the component of the vertical direction of section B of the second graph 950, a value greater than 0 indicates the occurrence of the acceleration in a direction opposite to gravity. The processor 120 may detect whether the electronic device 101 has fallen, based on the difference value between the gravity direction features.

FIG. 10 is a flowchart 1000 illustrating a method for performing a third misrecognition improvement process in an electronic device according to an embodiment. FIG. 10 may illustrate steps 305 and 307 of FIG. 3 in detail. The flowchart 1000 of FIG. 10 may correspond to the third misrecognition improvement process.

Referring to FIG. 10, in step 1001, a processor of an electronic device may identify an impact timepoint. The processor 120 may obtain an acceleration magnitude by using a local frame value (for example, the x-axis, y-axis, and z-axis coordinates) of acceleration sensing data. The processor 120 may obtain an acceleration magnitude from Equation (1). The processor 120 may determine a timepoint when a large variation in the acceleration magnitude occurs for a short time as an impact timepoint. When the user rapidly lowers the arm from top to bottom while wearing the electronic device 101, such as by striking downward on a table with the fist, or the user has a fall accident, a variation in the acceleration magnitude may be large.

In step 1003, the processor 120 may identify a pre-impact time, with reference to the impact timepoint. The processor 120 may identify a predetermined time before the impact timepoint (for example, 3 seconds or 5 seconds before the impact timepoint) as "a pre-impact time". I processor 120 may extract a section with little movement from the pre-impact time. For example, when the pre-impact time is 5 seconds, the processor 120 may extract a section (for example, 1 second) with little movement from 5 seconds. The extraction of the section with little movement may increase the accuracy when determining the user's fall.

In step 1005, the processor 120 may calculate position information within the pre-impact time. In addition, the processor 120 may calculate the position information in the section with little movement within the pre-impact time. The position information may include at least one of roll, yaw, or pitch. The roll or pitch may include a value representing gravity and the yaw may include a value representing the directivity. The yaw is required for the accuracy of the position information, but the yaw may not be obtained by the acceleration sensing data alone.

In order to improve misrecognition related to the user's fall, and may not require the yaw representing the directivity. The processor 120 may calculate the position information, based on the acceleration sensing data having been acquired by the acceleration sensor. For example, the processor 120 may calculate the roll and the pitch to obtain the position information, based on the acceleration sensing data.

In step 1007, the processor 120 may determine whether the position information has a value exceeding a position threshold. The position threshold may be configured in the electronic device 101, based on a value measured when the user falls. A memory of the electronic device 101 may store a position threshold. The processor 120 may perform step 1009 when the position information has a value exceeding the position threshold, and perform step 1013 when the position information has a value less than or equal to the position threshold.

The position threshold may include at least one of a roll threshold, a pitch threshold, and a yaw threshold. The processor 120 may determine whether the roll included in the position information has a value exceeding a roll threshold and the pitch included in the position information has a value exceeding a pitch threshold. The processor 120 may perform step 1009 when each of the roll and the pitch has a value exceeding the threshold, and perform step 1013 when at least one of the roll or the pitch has a value less than or equal to the threshold.

In step 1009, the processor 120 may calculate the maximum amount of atmospheric pressure variation. The processor 120 may identify a predetermined time section after the impact timepoint (for example, 3 seconds or 5 seconds after the impact timepoint) as "a post-impact time". The processor 120 may obtain the maximum amount of atmospheric pressure variation for the post-impact time, based on the atmospheric pressure sensing data having been acquired by the atmospheric pressure sensor. The maximum amount of atmospheric pressure variation may be expressed in a peak-to-peak form. The processor 120 may obtain the maximum amount of atmospheric pressure variation for a predetermined time before and after the impact timepoint or at the impact timepoint.

In step 1011, the processor 120 may determine whether the maximum amount of atmospheric pressure variation exceeds a variation threshold. The processor 120 may perform step 1015 when the maximum amount of atmospheric pressure variation is less than a variation threshold, and perform step 1013 when the maximum amount of atmospheric pressure variation is greater than or equal to a variation threshold.

A third misrecognition improvement process of FIG. 10 may be configured to sense misrecognition of when the user rapidly lowers the hand from top to bottom while wearing the electronic device 101. The third misrecognition improvement process may be configured to sense misrecognition in when the user raises the hand over the head and then hits down a table while sitting or the user raises the hand over the head and then rapidly lowers the hand while standing. The maximum amount of atmospheric pressure variation when the user rapidly lowers the hand from top to bottom may be less than the maximum amount of atmospheric pressure variation in the user's actual fall accident.

In step 1013, the processor 120 may determine that the user has had a fall accident when position information has a value less than or equal to a position threshold. The processor 120 may determine that the user has had a fall accident when position information has a value exceeding a position threshold and the maximum amount of atmospheric pressure variation is greater than or equal to a variation threshold. The processor 120 may perform step 309 of FIG. 3 when it is determined that the user has had a fall accident. In addition, the processor 120 may perform a fourth misrecognition improvement process when a situation is determined as the user's fall accident by the third misrecognition improvement process. Referring to FIG. 12, the processor 120 may omit step 1201 when performing the fourth misrecognition improvement process after performing the third misrecognition improvement process.

Returning to FIG. 10, in step 1015, the processor 120 may determine that the electronic device 101 has fallen. When position information has a value exceeding a position threshold and the maximum amount of atmospheric pressure variation is less than a variation threshold, the processor 120 may determine that the electronic device 101 has fallen. When a situation is determined as the falling of the electronic device 101 by the third misrecognition improvement process, the processor 120 so as to acquire acceleration sensing data and atmospheric pressure sensing data in real time or periodically and thus determine whether the user has had a fall accident.

Figure 11A:
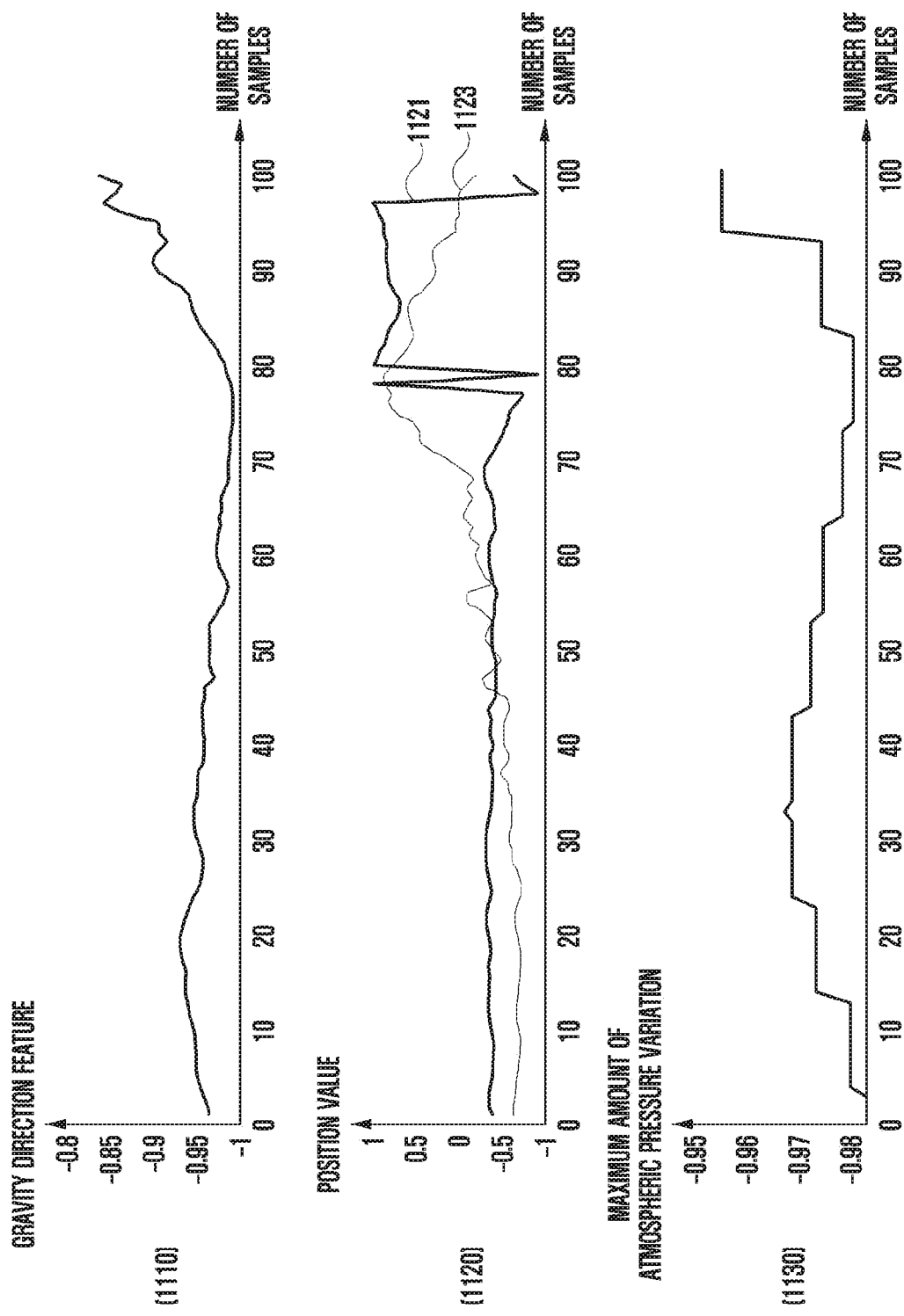
FIG. 11A illustrates a sensor graph related to a third misrecognition improvement process.
Figure 11B:
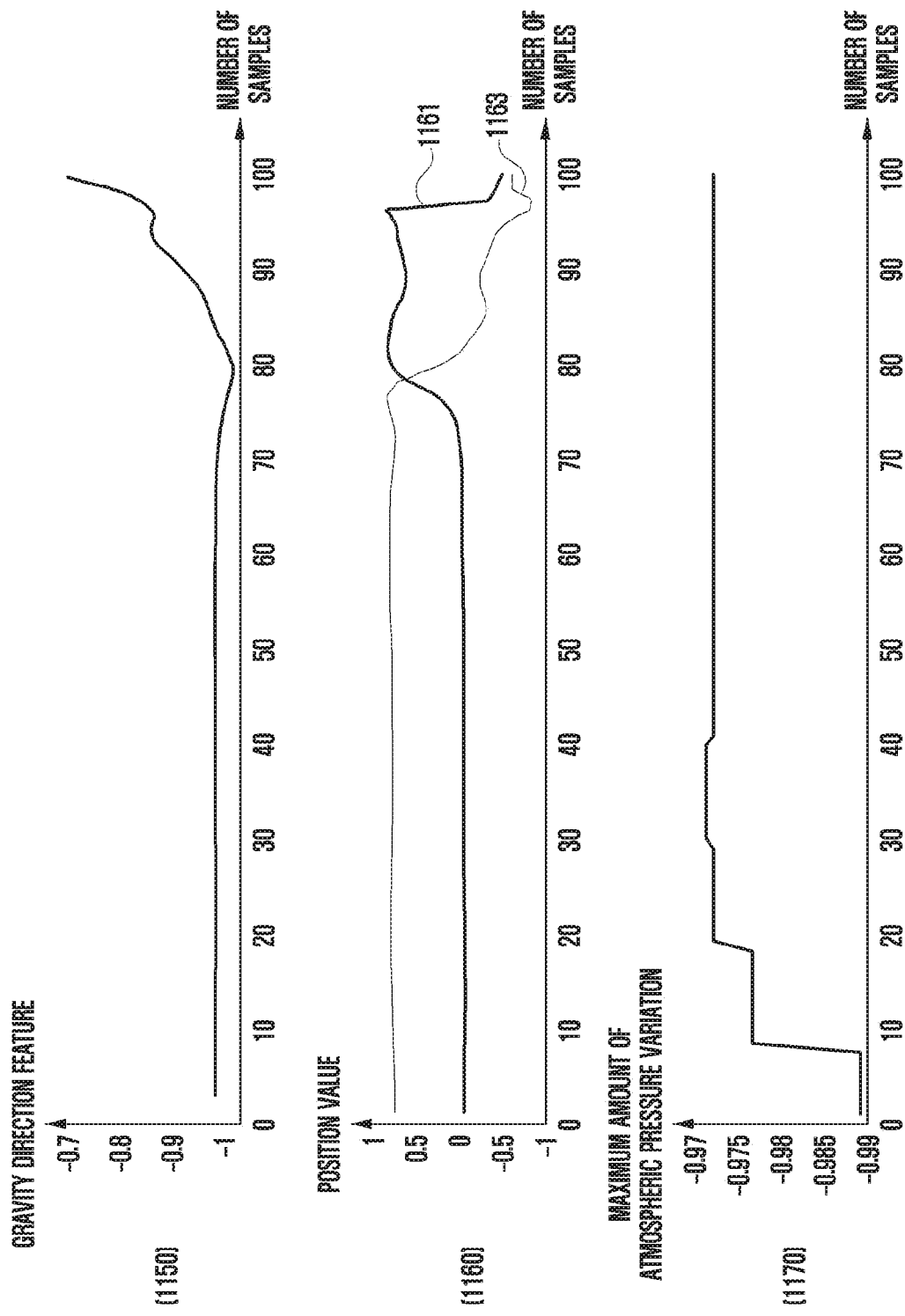
FIG. 11B illustrates a sensor graph related to a third misrecognition improvement process according to an embodiment.

FIG. 11A illustrates a sensor graph related to a third misrecognition improvement process according to an embodiment. FIG. 11B illustrates a sensor graph related to a third misrecognition improvement process according to an embodiment.

First, second, and third graphs 1110, 1120, and 1130 of FIG. 11A may indicate graphs obtained by the measurement when the user has a fall accident. Fourth, fifth, and sixth graphs 1150, 1160, and 1170 of FIG. 11B may indicate graphs obtained by the measurement when the user lowers the hand from top to bottom while wearing the electronic device 101 (for example, when the user hits his or her hand or fist down on a table). The x-axis of each of the first graph 1110 to the sixth graph 1170 may indicate the number of samples, one interval of the x-axis may indicate one sample, and a time unit of one sample may be 10 msecs.

Referring to FIGS. 11A and 11B, the first graph 1110 and the fourth graph 1150 present a gravity direction feature. In the first graph 1110 and the fourth graph 1150, a timepoint (for example, the 100th sample) representing the peak of the gravity direction feature may be an impact timepoint. It is noted from the comparison between the first graph 1110 and the fourth graph 1150 that a gravity direction feature when a fall accident occurs is similar to a gravity direction feature when the user artificially moves the electronic device 101 downwards. That is, the gravity direction feature alone may not distinguish the user's fall accident and the falling of the electronic device 101. To this end, the processor 120 of the electronic device 101 may calculate position information or the maximum amount of atmospheric pressure variation, with reference to the impact timepoint, and thus determine whether the user has fallen.

The second graph 1120 and the fifth graph 1160 represent position information. In the second graph 1120, a first signal 1121 may represent roll (or a roll value) included in position information, and a second signal 1123 may represent pitch (or a pitch value) included in position information. In addition, in the fifth graph 1160, a first signal 1161 may represent roll (or a roll value) included in position information, and a second signal 1163 may represent pitch (or a pitch value) included in position information. It is noted from the comparison between the second graph 1120 and the fifth graph 1160 that variations in the roll and the pitch are large even before the impact timepoint (for example, 100 nanoseconds), but variations in the roll and the pitch when a fall accident occurs are different from variations in the roll and the pitch when the user artificially moves the electronic device 101 downwards The processor 120 may calculate position information for a predetermined time, such as a 60th sample to the 100th sample before the impact timepoint and thus determine whether the user has fallen, based on whether the position information has a value exceeding a position threshold. It is noted from the comparison between the second graph 1120 and the fifth graph 1160 that each of the roll and the pitch when a fall accident occurs has a value less than or equal to a threshold, but each of the roll and the pitch when the user artificially moves the electronic device 101 downwards has a value exceeding a threshold. The processor 120 may determine whether the user has fallen, based on whether position information has a value exceeding a position threshold.

The third graph 1130 and the sixth graph 1170 represent the maximum amount of atmospheric pressure variation. It is noted that in the third graph 1130, the maximum amount of atmospheric pressure variation has a variation of atmospheric pressure, which is similar to the gravity direction feature, while in the sixth graph 1170, the maximum amount of atmospheric pressure variation may have a variation of atmospheric pressure regardless of the gravity direction feature. For example, in the sixth graph 1170, the maximum amount of atmospheric pressure variation is large even in a 10th sample to the 80th sample having no variation in the gravity direction feature. Even considering that a delay occurs in atmospheric pressure sensing data in comparison to acceleration sensing data, the maximum amount of atmospheric pressure variation may be large regardless of the gravity direction feature when the user artificially moves the electronic device 101 downwards. The processor 120 may determine whether the user has fallen, based on the position information and the maximum amount of atmospheric pressure variation for the post-impact time.

FIG. 12 is a flowchart 1200 illustrating a method for performing a fourth misrecognition improvement process in an electronic device according to an embodiment. FIG. 12 may illustrate steps 305 and 307 of FIG. 3 in detail. The flowchart 1200 of FIG. 12 may correspond to a fourth misrecognition improvement process.

Referring to FIG. 12, in step 1201, a processor of an electronic device may identify an impact timepoint. The processor 120 may obtain an acceleration magnitude by using a local frame value (for example, the x-axis, y-axis, and z-axis coordinates) of acceleration sensing data. The processor 120 may obtain an acceleration magnitude from Equation (1). The processor 120 may determine a timepoint when a large variation in the acceleration magnitude occurs for a brief time as an impact timepoint. When the user rapidly lowers the arm while wearing the electronic device 101 or a fall accident occurs, a variation in the acceleration magnitude may be large.

In step 1203, the processor 120 may divide a post-impact time into segments, with reference to the impact timepoint. The processor 120 may identify a predetermined time after the impact timepoint (for example, 3 seconds or 5 seconds after the impact timepoint) as "a post-impact time". The processor 120 may divide a post-impact time into segments.

In step 1205, the processor 120 may calculate acceleration distribution for each segment. The acceleration distribution may be a value representing a dispersion degree of acceleration sensing data. The acceleration sensing data is a local frame value corresponding to a relative coordinate system, and for example, may have x-axis, y-axis, and z-axis coordinates. The processor 120 may calculate acceleration distribution for each segment, based on the acceleration sensing data having been acquired for the post-impact time.

When the user lies down on a soft surface such as a trampoline or a bed while wearing (or holding) the electronic device 101, a variation in the acceleration or the atmospheric pressure, which is similar to the user's actual fall accident, may occur. After the user's actual fall accident, when the user moves the arm to shift the position, an additional acceleration pattern may occur, and this acceleration pattern may be similar to an acceleration pattern when the user falls down on a soft surface.

In order to improve misrecognition related to the user's fall, the processor 120 may determine whether a variation in the acceleration or the atmospheric pressure, which has been detected by the performance of the fourth misrecognition improvement process, corresponds to fall misrecognition. The processor 120 may distinguish whether the sensing data having been detected from the acceleration distribution for each segment and the degree of atmospheric pressure variation results from the user's actual fall accident or results from when the user lies down on a soft surface.

In step 1207, the processor 120 may calculate an average acceleration distribution for the post-impact time by using the calculated acceleration distribution. The processor 120 may obtain an average value of the acceleration for the post-impact time from the average acceleration distribution. Step 1207 may be omitted.

In step 1209, the processor 120 may count the number of segments having the acceleration distribution having a value greater than or equal to a configured threshold. The processor 120 may count the number of segments having the acceleration distribution having a value greater than or equal to a configured threshold in the acceleration distribution for each segment included in the post-impact time. For example, the configured threshold is a reference value related to the acceleration distribution, and may be configured from the average acceleration distribution or previously configured in the electronic device 101. The configured threshold may be greater than the average acceleration distribution.

In step 1211, the processor 120 may calculate a degree of atmospheric pressure variation (or an atmospheric pressure varying velocity) for the post-impact time. The degree of atmospheric pressure variation may be expressed by a gradient and indicate a gradient of atmospheric pressure variation for a predetermined time.

In step 1213, the processor 120 may count the number of valleys of the degree of atmospheric pressure variation. A valley of the degree of atmospheric pressure variation may indicate where the gradient of atmospheric pressure varies, such as a part (or a timepoint) in which the overall rising gradient of atmospheric pressure descends and re-ascends. The processor 120 may count the number of valleys of the degree of atmospheric pressure variation for the post-impact time.

In step 1215, the processor 120 may determine whether the counted number of segments exceeds a distribution reference value and the counted number of valleys exceeds a valley reference value. The processor 120 may perform step 1217 when the counted number of segments is less than or equal to a distribution reference value or the counted number of valleys is less than or equal to a valley reference value. The processor 120 may perform step 1219 when the counted number of segments exceeds a distribution reference value and the counted number of valleys exceeds a valley reference value.

The processor 120 may further determine whether an average acceleration distribution has a value exceeding the configured threshold. The processor 120 may perform step 1217 when the average acceleration distribution has a value less than or equal to the configured threshold, the counted number of segments is less than or equal to a distribution reference value, or the counted number of valleys is less than or equal to a valley reference value. The processor 120 may perform step 1219 when the average acceleration distribution has a value exceeding the configured threshold, the counted number of segments exceeds a distribution reference value, and the counted number of valleys exceeds a valley reference value.

In step 1217, the processor 120 may determine that the user has had a fall accident when the counted number of segments is less than or equal to a distribution reference value or the counted number of valleys is less than or equal to a valley reference value. The processor 120 may determine that the user has had a fall accident when the average acceleration distribution has a value less than or equal to the configured threshold, the counted number of segments is less than or equal to a distribution reference value, or the counted number of valleys is less than or equal to a valley reference value. The processor 120 may perform step 309 of FIG. 3 when it is determined that the user has had a fall accident. Even when a situation is determined as the user's fall accident by the fourth misrecognition improvement process having been performed first, the processor 120 may perform first to third misrecognition improvement processes.

In step 1219, the processor 120 may determine that the electronic device 101 has fallen when the counted number of segments exceeds a distribution reference value and the counted number of valleys exceeds a valley reference value. The processor 120 may determine that the electronic device 101 has fallen when the average acceleration distribution has a value exceeding the configured threshold, the counted number of segments exceeds a distribution reference value, and the counted number of valleys exceeds a valley reference value. When a situation is determined as the falling of the electronic device 101 by the fourth misrecognition improvement process, the processor 120 returns to step 301 so as to acquire acceleration sensing data and atmospheric pressure sensing data in real time or periodically and thus determine whether the user has had a fall accident.

Figure 13B:
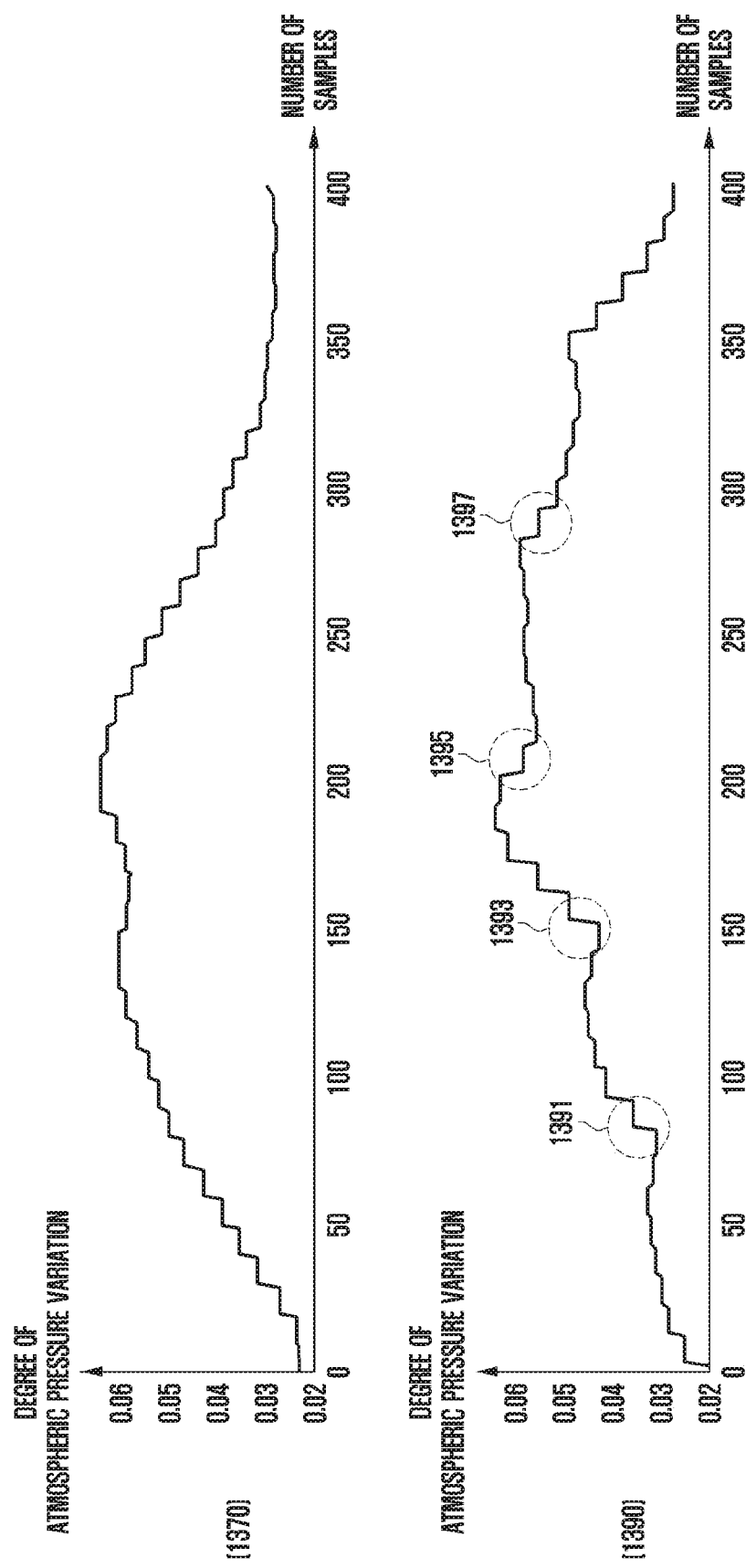
FIG. 13B illustrates a sensor graph related to a fourth misrecognition improvement process according to an embodiment.

FIG. 13A illustrates a sensor graph related to a fourth misrecognition improvement process according to an embodiment. FIG. 13B illustrates a sensor graph related to a fourth misrecognition improvement process according to an embodiment.

FIG. 13A illustrates a sensor graph related to when the user lies down on a soft surface.

Referring to FIG. 13A, a first graph 1310 represents the acceleration sensing data (or an acceleration value) having been acquired by the acceleration sensor. The x-axis of the first graph 1310 may indicate the number of samples and the y-axis thereof may indicate an acceleration value. One interval of the x-axis may indicate one sample, and a time unit of one sample may be 10 msecs. The acceleration sensing data of the first graph 1310 may include an x-axis signal 1311, a y-axis signal 1313, and a z-axis signal 1315, which correspond to a local frame. In the first graph 1310, timepoints 220 nsecs, 320 nsecs, and 400 nsecs representing the peak of the acceleration sensing data may be impact timepoints (or impact detection timepoints). It is noted from the first graph 1310 that there are three impact timepoints.

A second graph 1330 represents a gravity direction feature. The x-axis of the second graph 1330 may indicate the number of samples and the y-axis thereof may indicate a gravity direction feature. One interval of the x-axis may indicate one sample, and a time unit of one sample may be 10 msecs. The processor 120 may convert the acceleration sensing data of the first graph 1310 into a navigation frame. The processor 120 may extract a component with gravity having a value less than 0, as the gravity direction feature, from an upward value of the acceleration sensing data having been converted into the navigation frame. In the second graph 1330, timepoints 220 nsecs, 320 nsecs, and 400 nsecs representing the peak of the gravity direction feature may be similar to that of the first graph 1310.

A third graph 1350 represents atmospheric pressure sensing data (or an atmospheric pressure value) acquired by the atmospheric pressure sensor. The x-axis of the third graph 1350 may indicate the number of samples and the y-axis thereof may indicate the maximum amount of atmospheric pressure variation. One interval of the x-axis may indicate one sample, and a time unit of one sample may be 10 msecs. In the third graph 1350, timepoints including a first valley 1351, a second valley 1353, and a third valley 1355 representing the maximum amount of variation of the atmospheric sensing data may be impact timepoints. It is noted the first valley 1351, the second valley 1353, and the third valley 1355 have a change pattern similar to the impact timepoints of the first graph 1310 and the second graph 1330.

It is noted that the first valley 1351, the second valley 1353, and the third valley 1355 indicate timepoints when the maximum amount of atmospheric pressure variation descends and re-ascends while following an overall rising gradient. When the user lies down on a soft surface such as a trampoline or a bed while wearing (or holding) the electronic device 101, the user's body may move up and down several times. For this reason, it is noted that the maximum amount of atmospheric pressure variation increases, decreases, and re-increases, with reference to the impact timepoints of the first graph 1310 and the second graph 1330. The processor 120 may count the number of segments having the acceleration distribution of a value greater than or equal to a threshold configured for the post-impact time, based on a signal shown in the second graph 1330, and count the number of valleys of the degree of atmospheric pressure variation, so as to determine whether the electronic device 101 has fallen.

FIG. 13B illustrates a sensor graph illustrating the comparison between the user's fall accident and when the user lies down on a soft surface.

Referring to FIG. 13B, a fourth graph 1370 represents a degree of atmospheric pressure variation when the user has a fall accident. A fifth graph 1390 represents a degree of atmospheric pressure variation when the user lies down on a soft surface. The x-axis of each of the fourth graph 1370 and the fifth graph 1390 may indicate the number of samples and the y-axis thereof may indicate a degree of atmospheric pressure variation. One interval of the x-axis may indicate one sample, and a time unit of one sample may be 10 msecs.

It is noted from the fourth graph 1370 that, if the user's fall accident actually occurs, the degree of atmospheric pressure variation having continuously ascended descends. It is noted from the fifth graph 1390 that a first valley 1391, a second valley 1393, a third valley 1395, and a fourth valley 1397, where a gradient of the degree of atmospheric pressure variation varies according to the user's vertical movement when the user lies down on a soft surface, appear several times. The processor 120 may determine that the electronic device 101 has fallen, based on whether a variation value, such as the number of valleys of the degree of atmospheric pressure variation of the gradient of the degree of atmospheric pressure variation exceeds a reference value.

Figure 14:
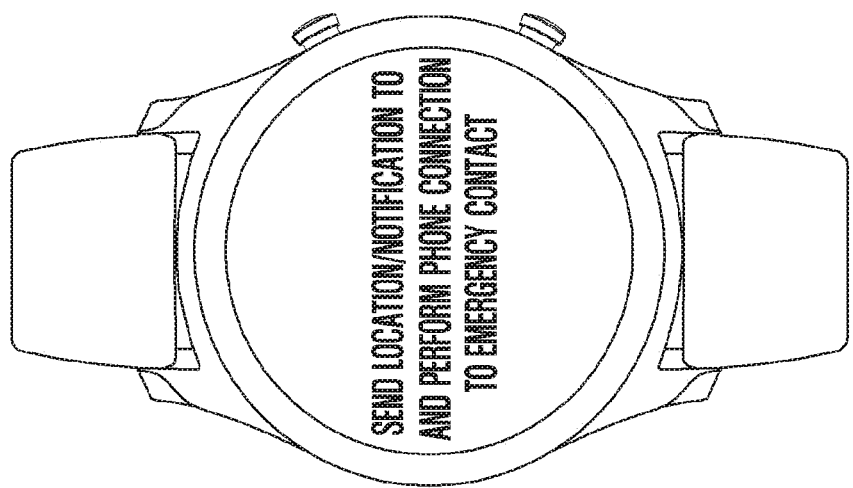
FIG. 14 illustrates an example of a user interface associated with a fall accident according to an embodiment.
Figure 14:
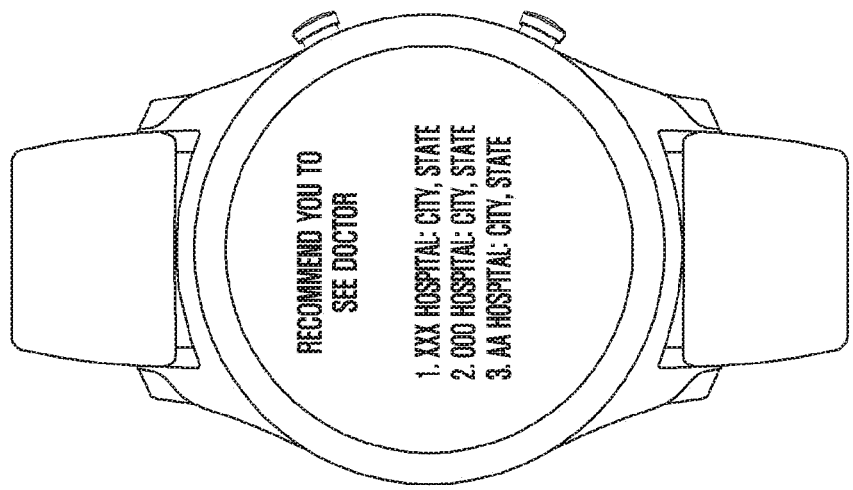
Figure 14:
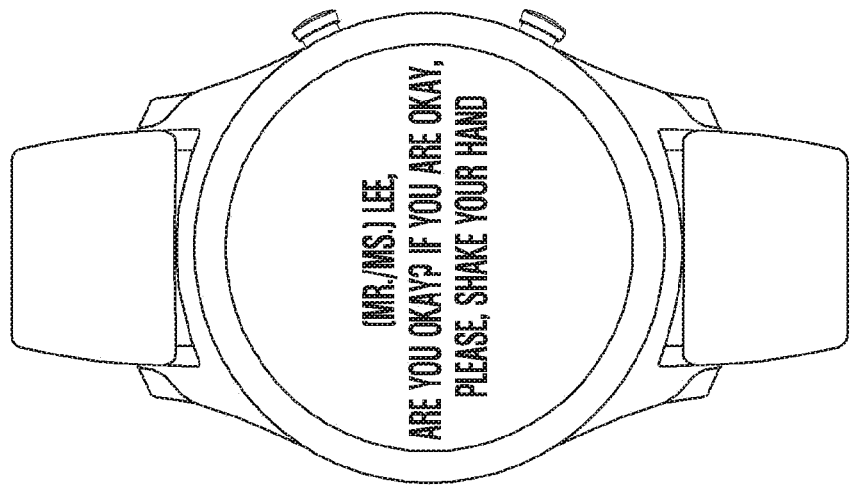

FIG. 14 illustrates an example of a user interface associated with a fall accident according to an embodiment.

Referring to FIG. 14, a processor of an electronic device may provide a user interface 1410, 1430 or 1450 as a notification related to a fall accident. The processor 120 may display the user interface related to a fall accident on a display. The user interface may include at least one of text, an image, or a video. The processor 120 may provide the notification related to a fall accident through a speaker or vibration.

The first user interface 1410 may be configured to identify if a fall accident occurs. For example, the processor 120 may provide the first user interface 1410 when it is determined that the user has had a fall accident in step 309 of FIG. 3. The processor 120 may output a vibration or a voice such as a warning sound while displaying the first user interface 1410 on the display. The first user interface 1410 may be a notification to be provided when the electronic device 101 is a wearable device that can be worn around the user's wrist. The processor 120 may display the first user interface 1410 and then sense (or detect) whether the motion which shakes the electronic device 101 is detected. The processor 120 may detect the movement of the electronic device 101 by using a motion sensor.

The processor 120 may provide the second user interface 1430 when the motion of shaking the electronic device 101 is detected, and provide the third user interface 1450 when the motion of shaking the electronic device 101 is not detected. The processor 120 may determine that the user is conscious and provide the second user interface 1430 when the user shakes the electronic device 101 after a fall accident. The second user interface 1430 may be configured to inform the user of what to do if a fall accident occurs. The second user interface 1430 may provide a hospital list (for example, 1. XXX hospital, 2. OOO hospital, and 3. AA hospital), based on a current location of the electronic device 101, such as address, city and state. The hospital list may be arranged according to distance from the current location with the closest hospital being provided first, or according to the time it takes for a patient to be brought to the hospital with the hospital having the shortest patient transit time being provided first in consideration of current traffic conditions. Otherwise, the hospital list may include hospitals specializing in fall accidents, which are arranged according to distance from the current location with the closest hospital being provided first.

The processor 120 may determine that the user is not conscious and provide the third user interface 1450 when the user does not shake the electronic device 101 after a fall accident. The third user interface 1450 may be configured to report the occurrence of a fall accident to the outside. The third user interface 1450 may be configured to report the occurrence of a fall accident and a current location of the electronic device 101 to a safety report center or emergency contact previously configured in the electronic device 101. The processor 120 may perform a phone connection to the safety report center after providing the third user interface 1450.

An operation method of an electronic device according to an embodiment may include acquiring acceleration sensing data from an inertia sensor included in the electronic device and atmospheric pressure sensing data from an atmospheric pressure sensor included in the electronic device, sensing whether the electronic device has fallen, based on the acceleration sensing data and the atmospheric pressure sensing data, and determining whether the user has fallen, based on the acceleration sensing data, when it is determined that the electronic device has fallen.

Sensing may include extracting a gravity direction feature from the acceleration sensing data, obtaining an atmospheric pressure varying velocity or the maximum amount of atmospheric pressure variation, based on the atmospheric pressure sensing data, and sensing whether the electronic device has fallen, based on at least one of the extracted gravity direction feature, the atmospheric pressure varying velocity, or the maximum amount of atmospheric pressure variation.

Sensing may include determining that the electronic device has fallen, based on the extracted gravity direction feature, when the electronic device moves with gravity, the atmospheric pressure varying velocity exceeds a velocity threshold, and the maximum amount of atmospheric pressure variation exceeds a variation threshold.

Sensing may include sensing the occurrence of the movement with gravity, with reference to the peak of the gravity direction feature, and determining that a fall has occurred in at least one of instances when the atmospheric pressure varying velocity exceeds a velocity threshold and the maximum amount of atmospheric pressure variation exceeds a variation threshold.

Determining may include obtaining an acceleration magnitude from the acceleration sensing data, detecting a gravity-free section, based on the acceleration magnitude, and determining whether the user has fallen, based on the gravity-free section, Determining may include determining that the electronic device has fallen when the gravity-free section has a value exceeding a section threshold, or determining that the user has had a fall accident when the gravity-free section has a value less than or equal to a section threshold.

Determining may include obtaining an acceleration magnitude from the acceleration sensing data, identifying an impact timepoint, based on the acceleration magnitude, extracting gravity direction features, based on the impact timepoint, calculating a difference value between the gravity direction features, and determining whether the user has fallen, based on the difference value.

When the user drops the electronic device or causes an artificial impact on the electronic device may be misrecognized as an actual fall, and thus whether a fall accident has occurred may be more accurately recognized from sensing data having been acquired by the inertia sensor and the atmospheric pressure sensor.

An electric current consumption may be reduced by monitoring whether a fall accident occurs in a low power state without increasing a sampling rate of a sensor.

A misrecognition rate of a fall accident may be reduced, based on at least one of the gravity direction feature, the atmospheric pressure varying velocity, and the maximum amount of atmospheric pressure variation.

The user's fall situation may be sensed without the sensing of an amount of impact which occurs when the user falls.

When the user rapidly lowers the arm from top to bottom while wearing the electronic device or the user falls down or lies down on a soft surface may be misrecognized as an actual fall, and thus whether a fall accident has occurred may be more accurately recognized from sensing data having been acquired by the inertia sensor and the atmospheric pressure sensor.

While the disclosure has been particularly shown and described with reference to certain embodiments thereof, it will be understood by those skilled in the art that various changes in form and details may be made therein without departing from the scope of the subject matter as defined by the appended claims and their equivalents.

What is claimed is:

1. An electronic device comprising:
    an inertia sensor;
    an atmospheric pressure sensor;
    a processor operatively connected to the inertia sensor, the atmospheric pressure sensor, and a memory; and
    the memory operatively connected to the processor,
    wherein the memory is configured to store instructions which, when executed, cause the processor to:
        acquire acceleration sensing data from the inertia sensor, wherein the acceleration sensing data acquired by the inertia sensor includes a local frame value corresponding to a relative coordinate system, and atmospheric pressure sensing data from the atmospheric pressure sensor;
        convert the acceleration sensing data from a local frame to a navigation frame;
        extract a value less than 0, as a gravity direction feature from an upward value of the acceleration sensing data converted into the navigation frame;
        sense the occurrence of movement of the electronic device with a direction of gravity, with reference to a peak of the gravity direction feature;
        sense whether the electronic device has fallen based on the acceleration sensing data and the atmospheric pressure sensing data;
        perform a first process for determining a fall accident based on a gravity-free section and a second process for determining a fall accident based on a difference value between gravity direction features after an impact timepoint, when it is determined that the electronic device has fallen; and
        determine a user has fallen, when it is determined that the fall accident has happened based on the first process and the second process.

2. The electronic device of claim 1, wherein the instructions further cause the processor to:
    obtain an atmospheric pressure varying velocity or a maximum amount of atmospheric pressure variation from the atmospheric pressure sensing data; and
    sense whether the electronic device has fallen, the atmospheric pressure varying velocity, and the maximum amount of atmospheric pressure variation.

3. The electronic device of claim 1, wherein the instructions further cause the processor to confirm that the electronic device has fallen based on the extracted gravity direction feature, when the electronic device moves with the direction of gravity, the atmospheric pressure varying velocity exceeds a velocity threshold, and the maximum amount of atmospheric pressure variation exceeds a variation threshold.

4. The electronic device of claim 1, wherein the instructions further cause the processor to:
    obtain an acceleration magnitude from the acceleration sensing data;
    detect the gravity-free section, based on the acceleration magnitude; and
    determine whether the user has fallen based on the gravity-free section.

5. The electronic device of claim 4, wherein the instructions further cause the processor to:
    determine that the electronic device has fallen when the gravity-free section has a value exceeding a section threshold; and
    determine that the user has had a fall accident when the gravity-free section has a value less than or equal to the section threshold.

6. The electronic device of claim 1, wherein the instructions further cause the processor to:
    obtain an acceleration magnitude from the acceleration sensing data;
    identify the impact timepoint, based on the acceleration magnitude;
    extract gravity direction features based on the impact timepoint;
    calculate a difference value between the gravity direction features; and
    determine whether the user has fallen based on the difference value.

7. The electronic device of claim 6, wherein the instructions further cause the processor to:
    determine that the electronic device has fallen when the difference value is less than or equal to a threshold; and
    determine that the user has had a fall accident when the difference value exceeds the threshold.

8. The electronic device of claim 1, wherein the instructions further cause the processor to:
    Determine the impact timepoint based on the acceleration sensing data;
    calculate position information for a pre-impact time based on the impact timepoint;
    calculate an amount of atmospheric pressure variation for a post-impact time, based on the impact timepoint; and
    determine that the electronic device has fallen when each of the position information and the amount of atmospheric pressure variation has a value exceeding a configured threshold.

9. The electronic device of claim 8, wherein the instructions further cause the processor to determine that the user has had a fall accident when the position information or the amount of atmospheric pressure variation has a value less than or equal to the configured threshold.

10. The electronic device of claim 1, wherein the instructions further cause the processor to:
    determine the impact timepoint based on the acceleration sensing data;
    divide a post-impact time into segments based on the impact timepoint;
    calculate acceleration distribution for each segment and count a number of segments having the acceleration distribution having a value greater than or equal to a configured threshold;
    calculate a degree of atmospheric pressure variation for the post-impact time and count a number of valleys of the degree of atmospheric pressure variation; and
    determine that the electronic device has fallen when the counted number of segments exceeds a distribution reference value and the counted number of valleys exceeds a valley reference value.

11. The electronic device of claim 10, wherein the instructions further cause the processor to:
calculate an average acceleration distribution for the post-impact time; and
determine that the electronic device has fallen when the average acceleration distribution has a value exceeding the configured threshold, the counted number of segments exceeds the distribution reference value, and the counted number of valleys exceeds the valley reference value.

12. The electronic device of claim 10, wherein the instructions further cause the processor to determine that the user has had a fall accident when the counted number of segments is less than or equal to the distribution reference value, or the counted number of valleys is less than or equal to the valley reference value.

13. The electronic device of claim 12, wherein the instructions further cause the processor to:
calculate an average acceleration distribution for the post-impact time; and
determine that the user has had a fall accident when the average acceleration distribution has a value less than or equal to the configured threshold, the counted number of segments is less than or equal to the distribution reference value, or the counted number of valleys is less than or equal to the valley reference value.

14. The electronic device of claim 1, further comprising:
a display;
a speaker; or
a vibration module,
wherein the instructions are configured to:
provide a notification related to a fall accident through at least one of the display, the speaker, and the vibration module when a situation is determined to be a fall accident,
detect whether the electronic device moves after providing the notification; and
provide different user interfaces based on a result of the detection of whether the electronic device moves,
wherein the electronic device is a wearable device.

15. An operation method of an electronic device, the method comprising:
acquiring acceleration sensing data from an inertia sensor included in the electronic device, wherein the acceleration sensing data acquired by the inertia sensor includes a local frame value corresponding to a relative coordinate system, and atmospheric pressure sensing data from an atmospheric pressure sensor included in the electronic device;
converting the acceleration sensing data from a local frame to a navigation frame;
extracting a value less than 0, as a gravity direction feature from the acceleration sensing data converted into the navigation frame;
sensing occurrence of movement of the electronic device with a direction of gravity, with reference to a peak of the gravity direction feature;
sensing whether the electronic device has fallen based on the acceleration sensing data and the atmospheric pressure sensing data; performing a first process for determining a fall accident based on a gravity-free section and a second process for determining a fall accident based on a difference value between gravity direction features after an impact timepoint, when it is determined that the electronic device has fallen; and
determining a user has fallen, when it is determined that the fall accident has happened based on the first process and the second process.

16. The method of claim 15, wherein sensing whether the electronic device has fallen comprises:
obtaining an atmospheric pressure varying velocity or a maximum amount of atmospheric pressure variation from the atmospheric pressure sensing data; and
sensing whether the electronic device has fallen based on at least one of the atmospheric pressure varying velocity and the maximum amount of atmospheric pressure variation.

17. The method of claim 16, wherein sensing whether the electronic device has fallen comprises:
confirming that the electronic device has fallen based on the extracted gravity direction feature, when the electronic device moves with the direction of gravity, the atmospheric pressure varying velocity exceeds a velocity threshold, and the maximum amount of atmospheric pressure variation exceeds a variation threshold.

* * * * *